(12) United States Patent
Long

(10) Patent No.: US 10,233,174 B2
(45) Date of Patent: Mar. 19, 2019

(54) THIOCARBAMATE PRODRUGS OF TOFACITINIB

(71) Applicant: THERAVANCE BIOPHARMA R&D IP, LLC, South San Francisco, CA (US)

(72) Inventor: Daniel D. Long, San Francisco, CA (US)

(73) Assignee: THERAVANCE BIOPHARMA R&D IP, LLC, South San Francisco, CA (US)

(*) Notice: Subject to any disclaimer, the term of this patent is extended or adjusted under 35 U.S.C. 154(b) by 0 days.

(21) Appl. No.: 15/986,018

(22) Filed: May 22, 2018

(65) Prior Publication Data
US 2018/0339980 A1 Nov. 29, 2018

Related U.S. Application Data

(60) Provisional application No. 62/509,852, filed on May 23, 2017, provisional application No. 62/544,318, filed on Aug. 11, 2017.

(51) Int. Cl.
| | | |
|---|---|---|
| *C07D 405/14* | (2006.01) | |
| *C07D 487/04* | (2006.01) | |
| *C07H 15/26* | (2006.01) | |
| *C12P 17/16* | (2006.01) | |
| *A61P 1/00* | (2006.01) | |
| *A61K 31/7028* | (2006.01) | |

(52) U.S. Cl.
CPC ........ *C07D 405/14* (2013.01); *A61K 31/7028* (2013.01); *A61P 1/00* (2018.01); *C07D 487/04* (2013.01); *C07H 15/26* (2013.01); *C12P 17/165* (2013.01)

(58) Field of Classification Search
CPC .... C07D 405/14; C07D 487/04; C07H 15/26; C12P 17/165; A61K 31/7028
USPC ........................................ 544/280; 514/265.1
See application file for complete search history.

(56) References Cited

U.S. PATENT DOCUMENTS

| | | |
|---|---|---|
| 5,811,388 A | 9/1998 | Friend et al. |
| RE41,783 E | 9/2010 | Blumenkopf et al. |
| 2011/0086810 A1 | 4/2011 | Rodgers et al. |
| 2011/0152207 A1 | 6/2011 | Goff et al. |
| 2012/0289571 A1 | 11/2012 | Zhao et al. |
| 2014/0357557 A1 | 12/2014 | Cole et al. |
| 2017/0145044 A1* | 5/2017 | Hudson .................. C07H 15/26 |
| 2018/0258094 A1 | 9/2018 | Long et al. |

FOREIGN PATENT DOCUMENTS

| | | |
|---|---|---|
| CN | 106496233 A | 3/2017 |
| WO | 93/22334 A1 | 11/1993 |
| WO | 2011/097987 A1 | 8/2011 |
| WO | 2011097087 A1 | 8/2011 |

OTHER PUBLICATIONS

Amidon et al., "Colon-targeted oral drug delivery systems: Design trends and approaches", AAPS PharmSciTech, 16 (4): 731-741 (2015).
Azad Khan et al., "Tissue and bacterial splitting of sulphasalazine", Clinical Science, 64: 349-354 (1983).
Bouvier et al., "First enzymatically activated Taxotere prodrugs designed for ADEPT and PMT", Bioorganic & Medicinal Chemistry, 12: 969-977 (2004).
Bunnelle, "Reagents for stereoselective preparation of N-carbamyl beta-D-glucuronides", The Journal of Organic Chemistry, 76: 5429-5432 (2011).
Burke et al., "Development of novel quaternary ammonium linkers for antibody-drug conjugates", Molecular Cancer Therapeutics, 15(5): 938-945 (May 2016).
Chourasia et al., "Pharmaceutical approaches to colon targeted drug delivery systems", J Pharm Pharmaceut Sci, 6 (1): 33-66 (2003).
Clark et al., "Discovery and development of Janus Kinase (JAK) inhibitors for inflammatory diseases", Journal of Medicinal Chemistry, 57: 5023-5038 (2014).
Danese, "New therapies for inflammatory bowel disease: from the bench to the bedside", Gut, 61: 918-932 (2012).
Friend et al., "A colon-specific drug-delivery system based on drug glycosides and the glycosidases of colonic bacteria", J Med Chem, 27: 261-266 (1984).

(Continued)

*Primary Examiner* — Venkataraman Balasubramanian
(74) *Attorney, Agent, or Firm* — Jeffrey A. Hagenah; Florence Jovic

(57) ABSTRACT

The invention relates to thiocarbamate prodrug compounds of the Janus kinase (JAK) inhibitor tofacitinib having formula I:

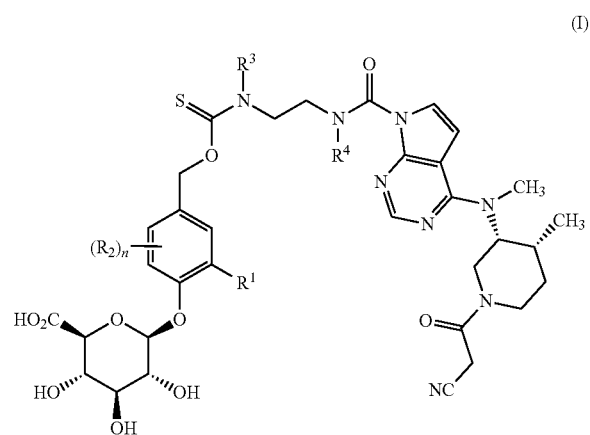

wherein $R^1$, $R^2$, $R^3$, $R^4$ and n are as defined. The invention also relates to pharmaceutical compositions comprising such compounds; methods of using such compounds to treat gastrointestinal inflammatory diseases; and processes and intermediates for preparing such compounds.

27 Claims, No Drawings

(56) References Cited

OTHER PUBLICATIONS

Friend et al., "Drug glycosides: Potential prodrugs for colon-specific drug delivery", J Med Chem, 28: 51-57 (1985).
Friend, "Glycosides in colonic drug delivery", Oral colon-specific drug delivery, pp. 153-187 (1992).
Goff et al., "Targeted delivery of vitamin D to the colon using beta-glucuronides of vitamin D: therapeutic effects in a murine model of inflammatory bowel disease", Am J Physiol Gastrointest Liver Physiol, 302: G460-G469 (2012).
Jeffrey et al., "Expanded utility of the beta-glucuronide linker: ADCs that deliver phenolic cytotoxic agents", ACS Medicinal Chemisty Letters, 1: 277-280 (2010).
Kagan et al., "Systems for region selective drug delivery in the gastrointestinal tract: biopharmaceutical considerations", Expert Opin Drug Deliv, 5(6): 681-692 (2008).
Kolakowski et al., "The methylene alkoxy carbamate self-immolative unit: utilization for the targeted delivery of alcohol-containing payloads with antibody-drug conjugates", Angew Chem Int Ed, 55: 1-5 (2016).
Kolakowski et al., "The methylene alkoxy carbamate self-immolative unit: utilization for the targeted delivery of alcohol-containing payloads with antibody-drug conjugates", Angew Chem Int Ed, 55: 1-5 Supporting Information (2016).
Lam et al., "Vedolizumab for ulcerative colitis and Crohn's disease: results and implications of GEMINI studies", Immunotherapy, 6(9): 963-971 (2014).
Lougerstay-Madec et al., "Synthesis of self-immolative glucuronide-based prodrugs of a phenol mustard", Anti-Cancer Drug Design, 13: 995-1007 (1998).
Mozaffari et al., "New biologic therapeutics for ulcerative colitis and Crohn's disease", Expert Opin Biol Ther, 14(5): 583-600 (2014).
Panes et al., "Randomized trial of tofacitinib in active ulcerative colitis: analysis of efficacy based on patient-reported outcomes", BMC Gastroenterology, 15: 14-23 (2015).
Philip et al., "Colon targeted drug delivery systems: A review on primary and novel approaches", Oman Medical Journal, 25(2): 70-78 (2010).
Sandborn et al., "Tofacitinib, an oral janus kinase inhibitor, in active ulcerative colitis", The New England Journal of Medicine, pp. 616-624 (2012).
Scheline, "Drug metabolism by intestinal microorganisms", Journal of Pharmaceutical Sciences, 57(12): 2021-2037 (1968).
Schmidt et al., "Glucuronide prodrugs of hydoxy compounds for antibody directed enzyme prodrug therapy (ADEPT): a phenol nitrogen mustard carbamate", Bioorganic & Medicinal Chemistry Letters, 7(8): 1071-1076 (1997).
Thomas et al., "Efficient regio- and stereoselective synthesis of 1-beta-O-glucuronyl carbamates and carbonates from unprotected 1,2,3,4-Hydroxyl glucuronates", Synlett, 12: 1966-1968 (2007).
Tranoy-Opalinski et al., "Beta-glucuronidase-responsive prodrugs for selective cancer chemotherapy: An update", European Journal of Medicinal Chemistry, 74: 302-313 (2014).
Wolk et al., "New targeting strategies in drug therapy of inflammatory bowel disease: mechanistic approaches and opportunities", Expert Opin Drug Deliv, 10(9): 1275-1286 (2013).
De Bont et al., "Synthesis and biological activity of beta-glucuronyl carbamate-based prodrugs of paclitaxel as potential candidates for ADEPT", Bioorganic & Medicinal Chemistry, 5(2): 405-414 (1997).
Fiorucci et al., "Enhanced activity of a hydrogen sulphide-releasing derivative of mesalamine (ATB-429) in a mouse model of colitis", British Journal of Pharmacology, 150: 996-1002 (2007).
Florent et al., "Prodrugs of anthracyclines for use in antibody-directed enzyme prodrug therapy", J Med Chem, 41: 3572-3581 (1998).
Heller et al., "Oxazolone coatis, a Th2 colitis model resembling ulcerative colitis, is mediated by IL-13-producing NK-T cells", Immunity, 17: 629-638 (Nov. 2002).
Kodela et al., "NOSH-aspirin: a novel nitric oxide-hydrogen sulfide-releasing hybrid: a new class of anti-inflammatory pharmaceuticals", ACS Med Chem Lett, 3: 257-262 (2012).
Lonnerholm et al., "Amount and distribution of carbonic anhydrases CA I and CA II in the gatrointestinal tract", Gastroenterology, 88: 1151-1161 (1985).
Schmidt et al., "Prodrug mono therapy: synthesis and biological evaluation of an etoposide glucuronide-prodrug", Bioorganic & Medicinal Chemistry, 11: 2277-2283 (2003).
Schmidt et al., "Cancer chemotherapy: a paclitaxel prodrug for ADEPT (antibody-directed enzyme prodrug therapy)", Eur J Org Chem, pp. 2129-2134 (2001).
Steiger et al., "Bio-orthogonal "click-and-release" donation of caged carbonyl sulfide (COS) and hydrogen sulfide (H2S)", Chem Commun, 53: 1378-1380 (2017).
Steiger et al., "Self-immolative thiocarbamates provide access to triggered H2S donors and analyte replacement fluorescent probes", J Am Chem Soc, 138: 7256-7259 (2016).
Tan et al., "New method for quantification of gasotransmitter hydrogen sulfide in biological matrices by LC-MS/MS", Nature, pp. 1-12 (2017).
Wallace et al., "Gastrointestinal safety and anti-inflammatory effects of a hydrogen sulfide-releasing diclofenac derivative in the rat", Gastroenterology, 132: 261-271 (2007).
Wallace et al., "Hydrogen sulfide-based therapeutics: exploiting a unique but ubiquitous gasotransmitter", Nature Reviews, 14: 329-345 (May 2015).
Angenault et al., "Cancer chemotherapy: A SN-38 (7-ethyl-10-hydroxycamptothecin)glucuronide prodrug for treatment by a PMT(prodrug montherapy)strategy", Bioorganic & Medicinal Chemistry Letters, 13: 947-950 (2003).
Desbene et al., "Application of the ADEPT strategy to the MDR resistance in cancer chemotherapy", Anti-cancer Drug Design, 14(2): 93-106 (1999).
Desbene et al., "Application of the ADEPT strategy to the MDR resistance in cancer chemotherapy", XP-002780712 (1999).
Goto et al., "Synthesis and biological activity of the metabolites of diethyl 4-[(4-bromo-2-cyanophenyl)carbamoyl] benzylphosphonate (NO-1886)", Chem Pharm Bull, 44(3): 547-551 (1996).
Kiss et al., "Synthesis and O.R.D./C.D. spectra of the anomers of 2-amino-5-ethoxyphenyl d-glucopyranosiduronic acid and some derivatives thereof", Carbohydrate Research, 12: 115-129 (1970).
Kreuzer et al., "Aufbau von oligosacchariden mit glycosylfluoriden unter lewissaure-katalyse", Carbohydrate Research, 149: 347-361 (1986).
Papot et al., "Design of selectively activated anticancer prodrugs: Elimination and cyclization strategies", Current Medicinal Chemistry, 2(2):155-185 (2002).
Schmidt et al., "Cancer chemotherapy: A paclitaxel prodrug for ADEPT (Antibody-directed enzyme prodrug therapy)", European Journal of Organic Chemistry, pp. 2129-2134 (2001).
Schmidt et al., "In vitro fluorine-19 nuclear magnetic resonance study of the liberation of antitumor nitrogen mustard from prodrugs", Royal Society of Chemistry, J. Chem. Soc., Perkin Transactions, 1:1302-1308 (2002).
Thomas et al., "Synthesis and biological evaluation of glucuronide prodrugs of the histone deacetylase inhibitor CI-994 for application in selective cancer chemotherapy", Bioorganic & Medicinal Chemistry, 16: 8109-8116 (2008).
U.S. Appl. No. 15/986,028, Long et al.
PCT International Preliminary Report and Written Opinion for PCT/US2018/033818 dated Aug. 9, 2018.
Kratky et al., "Synthesis and biological activity of new salicylanilide N,N-disubstituted carbamates and thiocarbamates", Bioorganic & Medicinal Chemistry, 22: 4073-4082 (2014).

* cited by examiner

THIOCARBAMATE PRODRUGS OF TOFACITINIB

CROSS-REFERENCE TO RELATED APPLICATIONS

This application claims the benefit of U.S. Provisional Application No. 62/509,852, filed on May 23, 2017, and 62/544,318, filed on Aug. 11, 2017, the disclosures of which are incorporated herein by reference in their entirety.

BACKGROUND OF THE INVENTION

Field of the Invention

This invention relates to thiocarbamate prodrug compounds of the Janus kinase (JAK) inhibitor tofacitinib. The invention also relates to pharmaceutical compositions comprising such compounds; methods of using such compounds to treat gastrointestinal inflammatory diseases; and processes and intermediates for preparing such compounds.

State of the Art

Tofacitinib is a Janus kinase (JAK) inhibitor having the chemical structure:

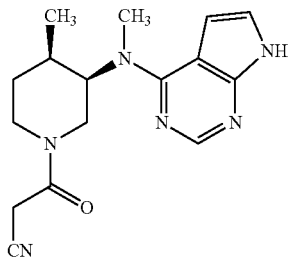

Tofacitinib and related compounds are described, e.g., in U.S. Reissue Patent No. RE41,783 E, as being useful as immunosuppressive agents for treating various medical conditions and disorders.

Tofacitinib (as the citrate salt) is approved in the U.S. and various other countries for the treatment of certain patients with moderately to severely active rheumatoid arthritis (RA). In clinical trials for tofacitinib, a number of systemically-mediated adverse events were reported including increased rates of serious infections, opportunistic infections, and malignancies; and laboratory abnormalities, such as lymphopenia, neutropenia, liver enzyme elevations, lipid elevations and serum creatinine elevations. As a result, the approved U.S. product (tradename XELJANZ®) carries a boxed warning detailing various safety risks, including the risk of serious infections and malignancies (see, XELJANZ/XEJANZ XR (tofacitinib) Prescribing Information, Pfizer Labs, New York, N.Y., Revised 2/2016). Additionally, the European Medicine Agency voted in 2013 not to recommend marketing authorization for tofacitinib in RA due to concerns about the overall safety profile of tofacitinib.

Tofacitinib has been studied in clinical trials for use in the treatment of ulcerative colitis (UC), a gastrointestinal inflammatory disease. See, e.g., Sandborn et al., *N. Engl. J. Med.*, 2011, 365, 1713-1725; and Panes et al., *BMC Gastroenterol*, 2015, 15, 14. If approved to treat UC, tofacitinib is expected to have systemically-mediated adverse events similar to those reported for RA.

U.S. application Ser. No. 15/358,462 (Theravance Biopharma) discloses glucuronide prodrugs of tofacitinib which have the advantage of limiting the systemic exposure of tofacitinib when treating localized inflammatory diseases. More specifically, when treating gastrointestinal inflammatory diseases, such as UC, these prodrugs increase the level of tofacitinib in the gastrointestinal tract while minimizing systemic exposure to tofacitinib.

Hydrogen sulfide ($H_2S$) has been shown to be a potent anti-inflammatory substance useful for various diseases including inflammatory gastrointestinal disorders. Endogenous $H_2S$ production appears to down-regulate leukocyte adherence to the vascular endothelium, a key early event in inflammation. In order to obtain a slow and specific release of $H_2S$, rather than an instantaneous bolus of the molecule, some slow-release donor compounds have been developed. For example, some $H_2S$-releasing small molecules have been shown in models of colitis and NSAID-induced gastritis to reduce the severity of these diseases. See e.g., Fiorucci et al., *British Journal of Pharmacology*, 2007, 150, 996-1002; Wallace et al., *Gastroenterology*, 2007, 132, 261-271; and Wallace et al., *Nature Reviews,* 2015, 14, 329-345.

Self-immolating thiocarbamate compounds have been shown to decompose and release carbonyl sulfide (COS) which is rapidly converted to $H_2S$ by the ubiquitous enzyme carbonic anhydrase. See, e.g., Steiger et al., *Chem. Comm.,* 2017, 53, 1378-1380 and *J. Am. Chem. Soc.,* 2016, 138, 7256-7259. Carbonic anhydrase has been shown to be highly expressed throughout the gastrointestinal tract (Lonnerholm et al., *Gastroenterology,* 1985, 88, 1151-1161).

It would be highly desirable to use a thiocarbamate prodrug to release COS and generate $H_2S$ locally in the gastrointestinal tract to treat a gastrointestinal inflammatory disease and avoid systemic release of $H_2S$ which may lead to toxicity.

Accordingly, it would be highly desirable to combine in a single molecule the ability to generate $H_2S$ and release tofacitinib in the gastrointestinal tract. For example, when treating gastrointestinal inflammatory diseases, such as UC, it would be highly desirable to administer a thiocarbamate prodrug having both the ability to generate $H_2S$ and release tofacitinib in the gastrointestinal tract while minimizing their systemic exposure.

SUMMARY OF THE INVENTION

In one aspect, the present invention provides novel glucuronide thiocarbamate prodrugs of tofacitinib which are designed to be cleaved by β-glucuronidase enzymes such as those produced by the microbiome in the gastrointestinal tract. Such cleavage generates $H_2S$ and releases tofacitinib in the gastrointestinal tract thereby increasing levels of both $H_2S$ and tofacitinib at the site of gastrointestinal inflammation and minimizing their systemic exposure.

The glucuronide thiocarbamate containing prodrugs of the present invention are sufficiently stable to be isolated, formulated in a pharmaceutical composition and administered to a patient in need of treatment. However, they are also sufficiently labile so as to be cleaved by β-glucuronidase and further break-down to efficiently release tofacitinib and generate $H_2S$.

In one aspect, the present invention relates to a compound of formula (I):

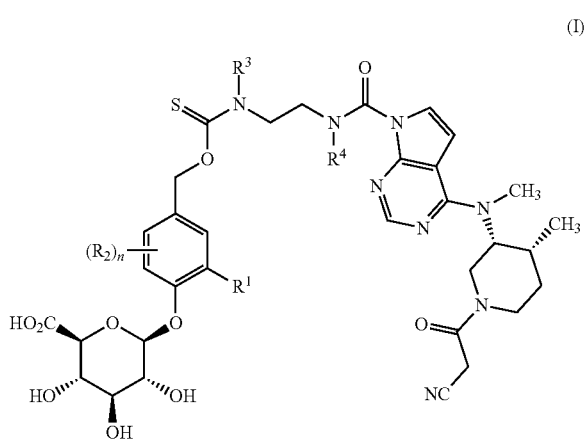

wherein n is 0, 1 or 2;

R¹ is selected from hydrogen, $C_{1-4}$ alkyl, $C_{1-3}$ alkoxy, amino, nitro, halo, cyano, hydroxy, and trifluoromethyl;

each R², when present, is independently selected from $C_{1-4}$ alkyl, $C_{1-3}$ alkoxy, amino, nitro, halo, cyano, hydroxyl, and trifluoromethyl;

R³ is selected from hydrogen, methyl and ethyl;

R⁴ is selected from hydrogen, methyl and ethyl;

or a pharmaceutically-acceptable salt thereof.

In another aspect, the present invention relates to a compound of formula (II):

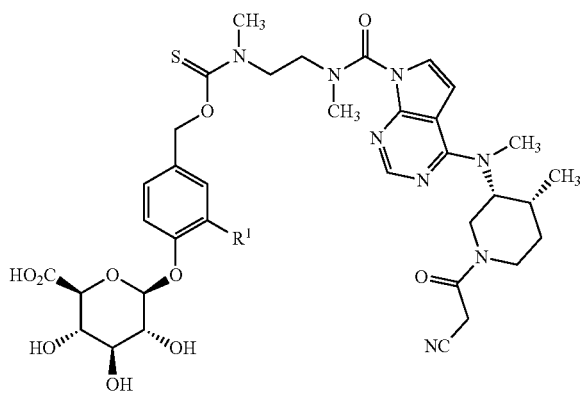

wherein

R¹ is selected from hydrogen, $C_{1-4}$ alkyl, $C_{1-3}$ alkoxy, amino, nitro, halo, cyano, hydroxy, and trifluoromethyl;

or a pharmaceutically-acceptable salt thereof.

In one embodiment, the invention provides a compound of formula (II) wherein R¹ is selected from hydrogen, methyl, methoxy, amino, nitro, and chloro, or a pharmaceutically-acceptable salt thereof.

In another aspect, the present invention relates to a compound of formula 1:

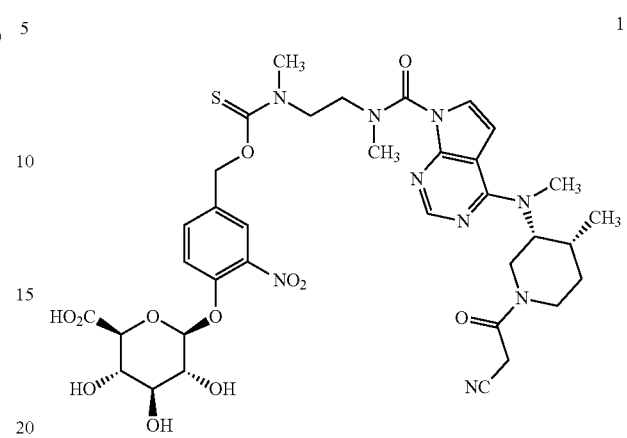

or a pharmaceutically acceptable salt thereof.

In another aspect, the present invention relates to a compound of formula 4:

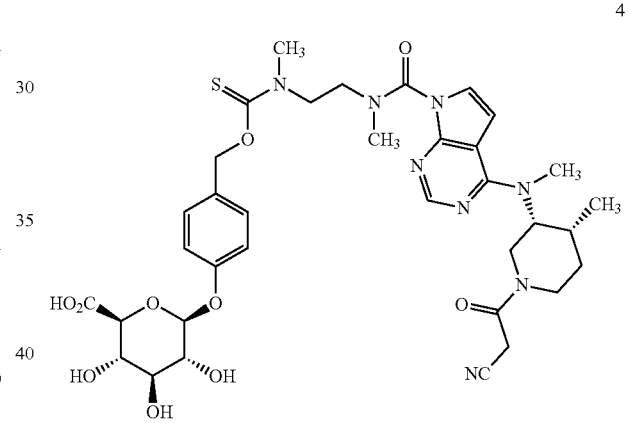

or a pharmaceutically acceptable salt thereof.

In one aspect, the compound of formula (I), (II) or 1 has low oral bioavailability and robust release of tofacitinib (2)

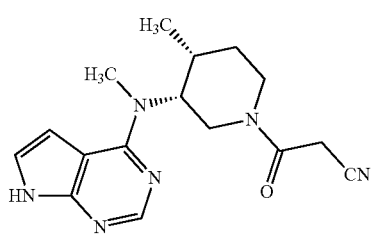

in vivo upon oral administration resulting in a marked increase in the ratio of colon exposure to plasma exposure relative to that obtained on oral dosing of tofacitinib itself.

In one embodiment, the compound of formula (I), (II), 1 or 4, produces tofacitinib or a salt thereof, upon contact with β-glucuronidase.

In one embodiment, the compound of formula (I), (II), 1 or 4, generates $H_2S$ in vivo upon contact with β-glucuronidase. In further embodiments, the compound of formula (I), (II), 1 or 4, produces carbonyl sulfide upon contact with β-glucuronidase and the carbonyl sulfide produced is converted to H₂S in vivo.

In one embodiment, the compound of formula (I), (II), 1 or 4, generates H₂S in vivo and produces tofacitinib or a salt thereof, upon contact with β-glucuronidase.

In another aspect, the present invention relates to a pharmaceutical composition comprising a pharmaceutically acceptable-carrier and a compound of formula (I), (II), 1 or 4, or a pharmaceutically acceptable salt thereof; or any specific embodiments thereof described herein.

In another aspect, the present invention relates to a method of treating a gastrointestinal inflammatory disease in a mammal, the method comprising administering to the mammal a pharmaceutical composition comprising a pharmaceutically acceptable-carrier and a compound of formula (I), (II), 1 or 4, or a pharmaceutically acceptable salt thereof; or any specific embodiments thereof described herein.

In one embodiment, the gastrointestinal inflammatory disease is ulcerative colitis. In another embodiment, the gastrointestinal inflammatory disease is Crohn's disease. And in another embodiment, the gastrointestinal inflammatory disease is colitis associated with immune checkpoint inhibitor therapy.

In another aspect, the present invention relates to a method of delivering tofacitinib and H₂S to the gastrointestinal tract of a mammal, in particular, to the colon, the method comprising orally administering to the mammal a thiocarbamate-containing prodrug of tofacitinib wherein the prodrug is cleaved to release tofacitinib and carbonyl sulfide and carbonyl sulfide is further converted to H₂S in vivo.

In one embodiment, the thiocarbamate-containing prodrug of tofacitinib contains a glucuronide moiety. In a further embodiment, the prodrug is cleaved by β-glucuronidase in the gastrointestinal tract to release tofacitinib and carbonyl sulfide. In a further embodiment, carbonyl sulfide is further converted to H₂S in vivo.

In one embodiment, tofacitinib and H₂S are delivered to the colon within a short time frame of each other. In further embodiments, tofacitinib and H₂S are delivered to the colon within 1, 5, 10, 15, 30, or 60 minutes of each other.

In separate and distinct embodiments, the thiocarbamate-containing prodrug of tofacitinib is a compound of formula (I), (II), 1 or 4, or a pharmaceutically acceptable salt thereof; or any specific embodiments thereof described herein.

In another aspect, the present invention relates to a process for preparing a compound of formula (I) or a pharmaceutically acceptable salt thereof, the process comprising deprotecting a compound of formula (I-A):

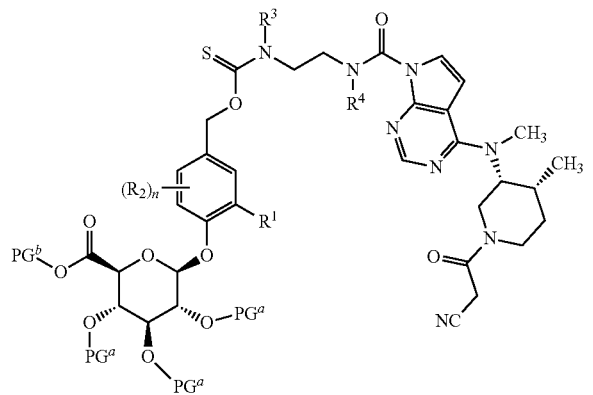

(I-A)

or a salt thereof; wherein $R^1$, $R^2$, $R^3$, $R^4$ and n are as defined herein; each $PG^a$ is independently a hydroxyl protecting group; and $PG^b$ is a carboxyl protecting group; to provide a compound of formula (I) or a pharmaceutically acceptable salt thereof.

In one embodiment of this process, $R^1$ is nitro; $R^3$ and $R^4$ are methyl; each $PG^a$ is acetyl; $PG^b$ is methyl; and n is 0.

In another aspect, the present invention relates to a compound of formula (I-A), or a salt thereof; or any specific embodiments thereof described herein.

In another aspect, the present invention relates to a process for preparing a compound of formula 1, or a pharmaceutically acceptable salt thereof, the process comprising:

(a) reacting a compound of formula 12'

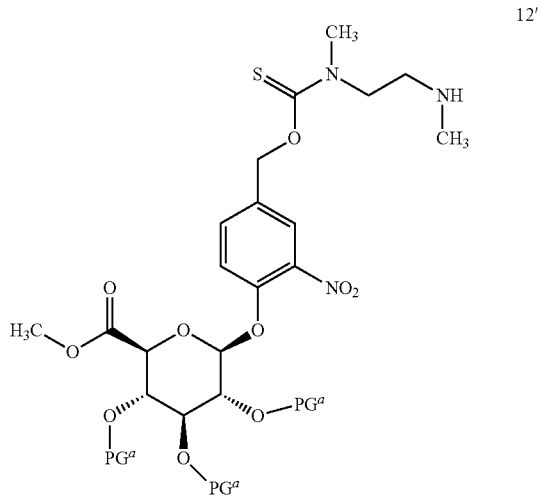

12' or a salt thereof; wherein each $PG^a$ is independently a hydroxyl protecting group, with a compound of formula 13

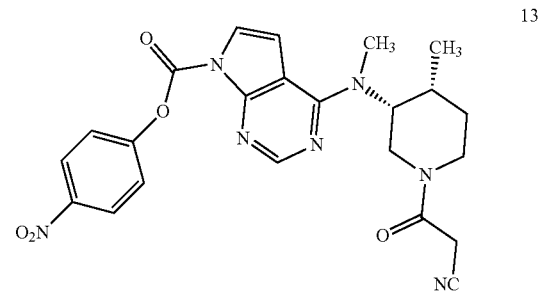 [SMILES: C[C@@H]1CCN(C(=O)CC#N)C[C@@H]1N(C)c1ncnc2c1ccn2C(=O)Oc1ccc([N+](=O)[O-])cc1]

13 to provide a compound of formula 14':

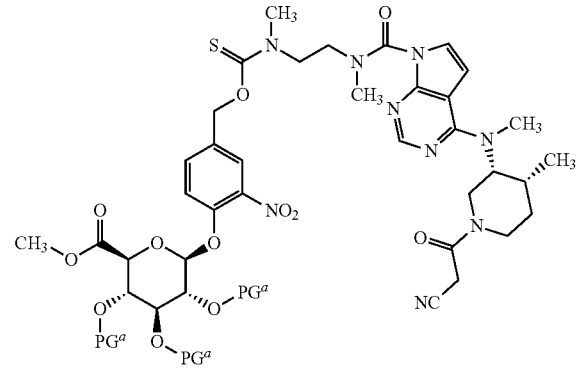

14' and (b) deprotecting the compound of formula 14' to provide the compound of formula 1 or a pharmaceutically acceptable salt thereof.

In one embodiment of this process, $PG^a$ is acetyl.

In separate and distinct aspects, the present invention also relates to a compound of formula 13, or a salt thereof; and a compound of formula 14' or a salt thereof, or any specific embodiments thereof described herein.

In another aspect, the present invention relates to a process for preparing a compound of formula 4, or a pharmaceutically acceptable salt thereof, the process comprising:

(a) reacting a compound of formula 18'

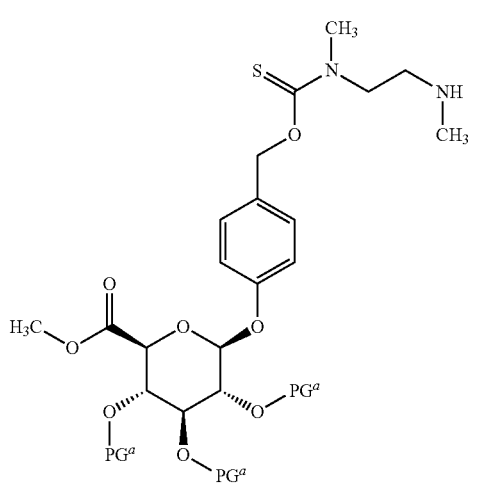

or a salt thereof; wherein each $PG^a$ is independently a hydroxyl protecting group, with a compound of formula 13

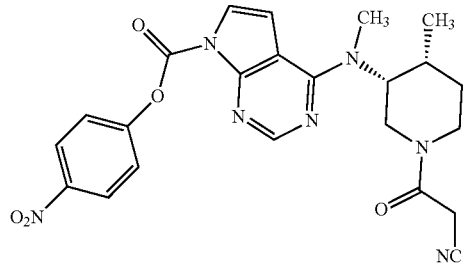

to provide a compound of formula 22':

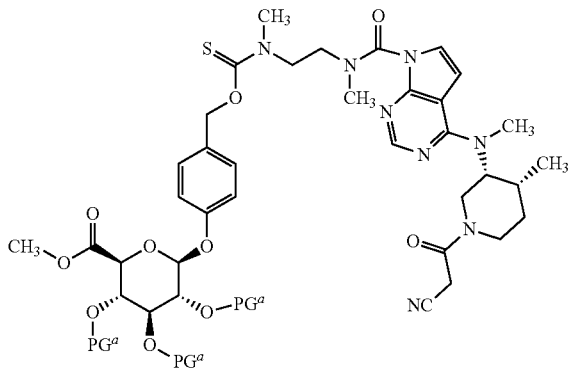

and (b) deprotecting the compound of formula 22' to provide the compound of formula 4 or a pharmaceutically acceptable salt thereof.

In one embodiment of this process, $PG^a$ is acetyl.

In separate and distinct aspects, the present invention also relates to a compound of formula 18', or a salt thereof; and a compound of formula 22' or a salt thereof, or any specific embodiments thereof described herein.

In separate and distinct aspects, the present invention also relates to other synthetic processes and intermediates described herein, which are useful for preparing the compounds of the invention.

In separate and distinct aspects, the present invention also relates to a compound of formula (I), (II), 1 or 4, or a pharmaceutically acceptable salt thereof; or any specific embodiments thereof described herein; for use in medical therapy; or for use in the manufacture of a medicament or a formulation. In one embodiment, the medicament or formulation is for treating a gastrointestinal inflammatory disease in a mammal.

Other aspects and embodiments of this invention are disclosed herein.

DETAILED DESCRIPTION OF THE INVENTION

Among other aspects, the invention provides thiocarbamate prodrugs of the JAK kinase inhibitor tofacitinib, pharmaceutically-acceptable salts thereof, and intermediates for the preparation thereof.

Chemical structures are named herein according to IUPAC conventions as implemented in ChemDraw software (PerkinElmer, Inc., Cambridge, Mass.). According to the convention, the compound of formula 1 may be identified as:

(2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl) carbamothioyl)oxy)methyl)-2-nitrophenoxy)-3,4,5-trihydroxytetrahydro-2H-pyran-2-carboxylic acid, while tofacitinib (2) may be identified as 3-((3R,4R)-4-methyl-3-(methyl(7H-pyrrolo[2,3-d]pyrimidin-4-yl)amino) piperidin-1-yl)-3-oxopropanenitrile, and the compound of formula 4 may be identified as:

(2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl) carbamothioyl)oxy)methyl)phenoxy)-3,4,5-trihydroxytetrahydro-2H-pyran-2-carboxylic acid.

The compounds of the invention contains multiple chiral centers. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Definitions

When describing this invention including its various aspects and embodiments, the following terms have the following meanings, unless otherwise indicated.

The singular terms "a," "an" and "the" include the corresponding plural terms unless the context of use clearly dictates otherwise.

The term "alkyl" means a monovalent saturated hydrocarbon group which may be linear or branched or combinations thereof. Unless otherwise defined, such alkyl groups typically contain from 1 to about 10 carbon atoms. Representative alkyl groups include, by way of example, methyl, ethyl, n-propyl, isopropyl, n-butyl, sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts derived from acids include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

Salts derived from pharmaceutically-acceptable inorganic bases include ammonium, calcium, magnesium, potassium, sodium, and zinc, and the like. Salts derived from pharmaceutically-acceptable organic bases include salts of arginine, choline, glucamine, lysine, benethamine, benzathine, betaine, 2-dimethylaminoethanol, 2-diethylaminoethanol, hydrabamine, morpholine, tromethamine, diethanolamine, ethanolamine, ethylenediamine, triethanolamine, 1H-imidazole, piperazine, and the like.

The term "salt thereof", as used herein, means an ionic compound in which a form of a compound of formula (I) is either the anion or cation of the ionic compound. For example, the anion of the ionic compound can be a carboxylate anion that is a deprotonated form of a compound of formula (I). The cation can be a protonated form of a compound of formula (I), i.e. a form where an amino group has been protonated by an acid. Typically, the salt is a pharmaceutically acceptable salt, although this is not required for salts of intermediate compounds that are not intended for administration to a patient.

Neutral compounds of formula (I) may optionally take the form of a zwitterion, where the term "zwitterion" means a neutral molecule with both positive and negative electrical charges.

The term "hydroxyl-protecting group" means a protecting group suitable for preventing undesired reactions at a hydroxyl group. Representative hydroxyl-protecting groups include, but are not limited to, alkyl groups, such as methyl, ethyl, and tert-butyl; allyl groups; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The term "carboxyl-protecting group" means a protecting group suitable for preventing undesired reactions at a carboxyl group. Representative carboxyl-protecting groups include, but are not limited to alkyl groups, such as methyl, ethyl, tert-butyl, and the like; arylmethyl groups, such as benzyl, 4-nitrobenzyl, 4-methoxybenzyl and the like; thiol groups, such as —S-tert-butyl and the like; silyl groups, such as trimethylsilyl, tert-butyldimethylsilyl and the like; oxazolines; and the like.

All other terms used herein are intended to have their ordinary meaning as understood by persons having ordinary skill in the art to which they pertain.

Representative Embodiments and Subgeneric Groupings

The following substituents and values are intended to provide representative examples of various aspects and embodiments of this invention. These representative values are intended to further define and illustrate such aspects and embodiments and are not intended to exclude other embodiments or to limit the scope of this invention.

In one embodiment, $R^1$ is hydrogen, $C_{1-4}$ alkyl, $C_{1-3}$ alkoxy, amino, nitro, halo, cyano, hydroxy, or trifluoromethyl. In another embodiment, $R^1$ is hydrogen, $C_{1-4}$ alkyl, $C_{1-3}$ alkoxy, amino, nitro, or chloro. In another embodiment, $R^1$ is hydrogen, methyl, methoxy, amino, nitro or chloro. In a particular embodiment, $R^1$ is hydrogen. In another particular embodiment, $R^1$ is nitro.

In one embodiment, n is 0. In another embodiment, n is 1. In another embodiment, n is 2.

When n is 1, in one embodiment, $R^2$ is $C_{1-4}$ alkyl, $C_{1-3}$ alkoxy, amino, nitro, halo, cyano, hydroxyl, or trifluoromethyl. In another embodiment, $R^2$ is $C_{1-4}$ alkyl, $C_{1-3}$ alkoxy, amino, nitro, fluoro or chloro. In another embodiment, $R^2$ is methyl, methoxy, amino, nitro, fluoro or chloro. In a particular embodiment, $R^2$ is fluoro.

When n is 1, the $R^2$ substituent may be in any available position of the phenyl ring to which $R^2$ is attached. In one embodiment, $R^2$ is ortho to $R^1$. In another embodiment, $R^2$ is meta to $R^1$. In another embodiment, $R^2$ is para to $R^1$.

When n is 2, in one embodiment, each $R^2$ is independently $C_{1-4}$ alkyl, $C_{1-3}$ alkoxy, amino, nitro, halo, cyano, hydroxyl, or trifluoromethyl. In another embodiment, each $R^2$ is independently $C_{1-4}$ alkyl, $C_{1-3}$ alkoxy, amino, nitro, fluoro or chloro. In another embodiment, each $R^2$ is independently methyl, methoxy, amino, nitro, fluoro or chloro. In a particular embodiment, each $R^2$ is fluoro.

When n is 2, the $R^2$ substituents may be in any available position of the phenyl ring to which $R^2$ is attached. In one embodiment, the $R^2$ substituents are ortho and meta to $R^1$. In another embodiment, the $R^2$ substituents are ortho and para to $R^1$. In another embodiment, the $R^2$ substituents are meta and para to $R^1$.

In one embodiment, $R^3$ is hydrogen. In another embodiment, $R^3$ is methyl. In another embodiment, $R^3$ is ethyl.

In one embodiment, $R^4$ is hydrogen. In another embodiment, $R^4$ is methyl. In another embodiment, $R^4$ is ethyl.

In one embodiment, both $R^3$ and $R^4$ are methyl. In another embodiment, one of $R^3$ and $R^4$ is hydrogen and the other is methyl.

In one embodiment, n is 0; $R^1$ is hydrogen, methyl, methoxy, amino, nitro or chloro; $R^3$ is methyl; and $R^4$ is methyl.

In another embodiment, n is 0; $R^1$ is hydrogen, methyl, methoxy, amino, nitro or chloro; $R^3$ is hydrogen; and $R^4$ is methyl.

In another embodiment, n is 0; $R^1$ is hydrogen, methyl, methoxy, amino, nitro or chloro; $R^3$ is methyl; and $R^4$ is hydrogen.

In another embodiment, n is 0; $R^1$ is hydrogen, methyl, methoxy, amino, nitro or chloro; $R^3$ is ethyl; and $R^4$ is ethyl.

In another embodiment, n is 1; $R^1$ is hydrogen, methyl, methoxy, amino, nitro or chloro; $R^2$ is methyl, methoxy, amino, nitro, fluoro or chloro; $R^3$ is methyl; and $R^4$ is methyl.

In another embodiment, n is 1; $R^1$ is hydrogen, methyl, methoxy, amino, nitro or chloro; $R^2$ is methyl, methoxy, amino, nitro, fluoro or chloro; $R^3$ is hydrogen; and $R^4$ is methyl.

In another embodiment, n is 1; $R^1$ is hydrogen, methyl, methoxy, amino, nitro or chloro; $R^2$ is methyl, methoxy, amino, nitro, fluoro or chloro; $R^3$ is methyl; and $R^4$ is hydrogen.

Synthetic Procedures

Compounds of formula (I) may be prepared according to the synthetic approach described in detail in the appended examples. As illustrated in Scheme 1 specifically for the preparation of the compound of formula 1, the key step of the synthesis is the formation of the urea linkage between tofacitinib and a protected form of the thiocarbamate glucuronide prodrug moiety 12'. In Scheme 1, $PG^a$ represents a hydroxyl protecting group, preferably allyl or acetyl, although other hydroxyl protecting group may also be used including a silyl protecting group such as tert-butyldimethylsilyl.

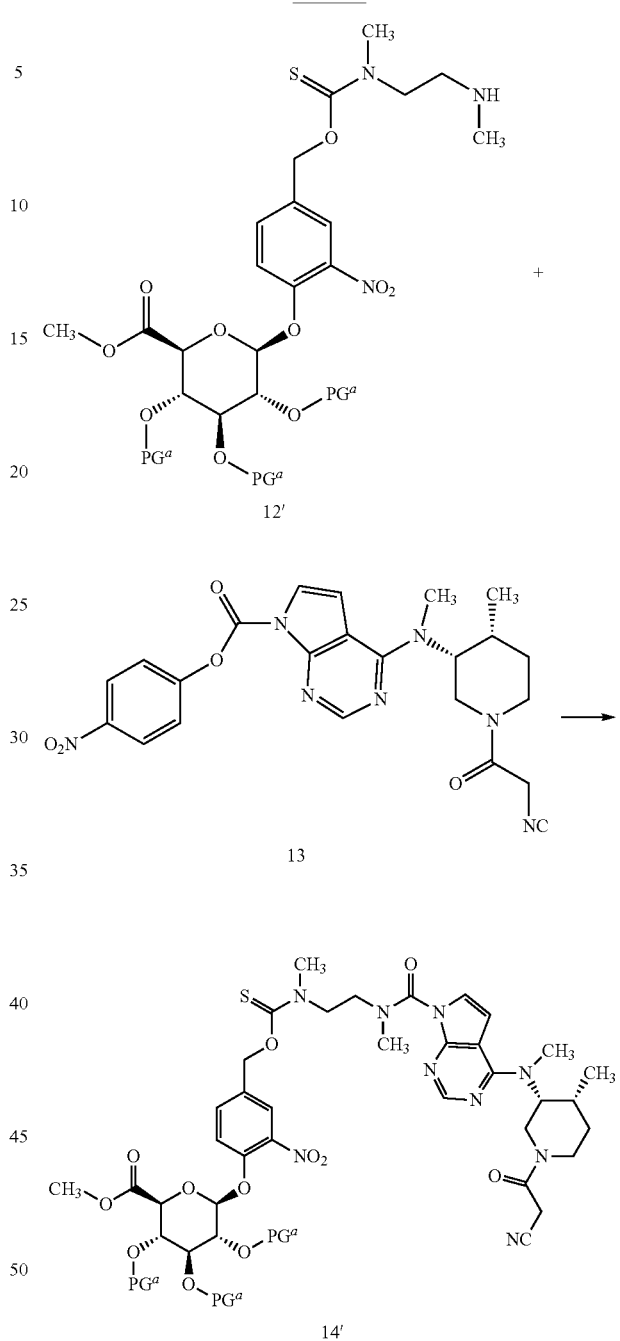

Preparations 1 to 4 and Example 1 describe the synthesis of compound 1 and various intermediates that were carried out. Applying the same synthetic methods with the appropriate substituents and starting materials is expected to lead to closely related structural analogs. Additionally, U.S. application Ser. No. 15/358,462 (Theravance Biopharma), which is hereby incorporated by reference in its entirety, describes the synthesis of compounds analogous to the compounds of this disclosure where the thiocarbamate moeity is replaced by a carbamate group. Applying the same synthetic methods where the carbamate is replaced by a thiocarbamate is expected to lead to the formation of the desired thiocarbamate analogs.

Accordingly, in one aspect, the invention provides a process of preparing compound 1, the process comprising (a) reacting a protected glucuronide thiocarbamate prodrug moiety 12' (which can be in a salt form) with an electrophilic tofacitinib derivative 13 to provide compound 14', and (b) deprotecting compound 14' to provide the compound of formula 1.

In one embodiment, compound 13 is formed by derivatizing tofacitinib with a reactive para-nitrophenyl or pentafluorophenyl moiety via a carbamate linkage. For example, para-nitrophenyl chloroformate, bis(4-nitrophenyl) carbonate, or bis(pentafluorophenyl) carbonate reagents can be used to form compound 13. The resulting protected intermediate 14' is deprotected, for example when $PG^a$ is an acetate group, with lithium hydroxide in a subsequent step to provide the compound of formula 1.

The action of a β-glucuronidase enzyme on the prodrugs of the invention is illustrated for the compound of formula 1. As shown in Scheme 2, upon action of a β-glucuronidase enzyme on the compound of formula 1, tofacitinib and carbonyl sulfide are expected to be released by a multistep process:

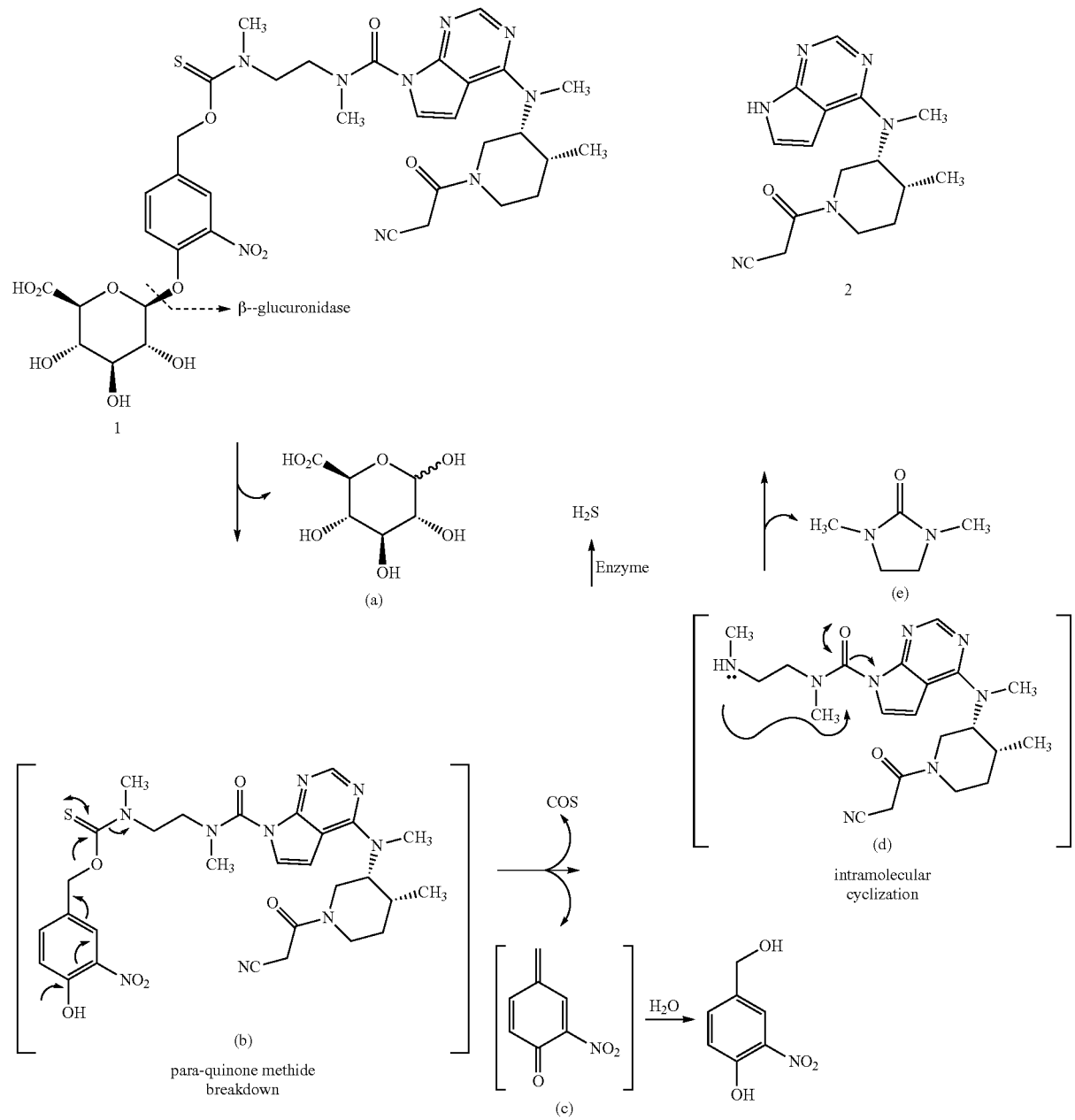

Scheme 2

In the initial step, the β-glucuronidase enzyme cleaves the glycosidic bond of the compound of formula 1, causing glucuronic acid (a) to be released and the formation of an aglycone intermediate (b). The aglycone spontaneously decomposes to afford a quinone methide species (c) which can be trapped with water, and a transient thiocarbamic acid which loses carbonyl sulfide (which is itself converted to $H_2S$ in vivo by the enzyme carbonic anhydrase) to afford a diamine (d). Intramolecular cyclization of the diamine leads to the formation of an imidazolidinone derivative (e) and release of tofacitinib.

Compound 1 was shown to release tofacitinib in the colon in an oral pharmacokinetics assay in mice (Assay 9). Additionally, Assay 11 demonstrates the ability of compound 1 to release $H_2S$ in an in-vitro model.

As described in the experimental section of the U.S. application Ser. No. 15/358,462 (Theravance Biopharma), the conversion of the carbamate analog of the compound of formula 1 to tofacitinib has been observed in incubations with purified β-glucuronidase and with freshly prepared rat colon content homogenate. U.S. application Ser. No. 15/358,462 (Theravance Biopharma) also showed that by comparison, the glucuronide prodrug approach did not appear to be applicable for delivering Mesalamine (5-aminosalicylic acid, 5-ASA) or 2-(5-fluoro-4-methylpyridin-3-yl)-5-(4-methyl-6-(methylsulfonyl)pyridin-3-yl)-1H-indole (a known CRAC inhibitor) directly to the colon.

The present evidence suggests the prodrugs of the invention are uniquely suited to take advantage of a β-glucuronidase-initiated breakdown mechanism to both release tofacitinib and produce $H_2S$ in the gastrointestinal tract.

Pharmaceutical Compositions

The compounds of the invention and pharmaceutically-acceptable salts thereof are typically used in the form of a pharmaceutical composition or formulation. Accordingly, in one of its compositions aspects, the invention is directed to a pharmaceutical composition comprising a pharmaceutically-acceptable carrier or excipient and a compound of formula (I), (II), 1 or 4, or a pharmaceutically-acceptable salt thereof. Optionally, such pharmaceutical compositions may contain other therapeutic and/or formulating agents if desired.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of a compound of formula (I), (II), 1 or 4, or a pharmaceutically acceptable salt thereof; including from about 5 to about 70% by weight; such as from about 10 to about 60% by weight of a compound of formula (I), (II), 1 or 4, or a pharmaceutically acceptable salt thereof.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending a compound of the invention with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of the present compounds calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the invention and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The following non-limiting examples illustrate representative pharmaceutical compositions of the present invention.

Tablet Oral Solid Dosage Form

A compound of the invention or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 4 mg, 10 mg or 20 mg active agent per tablet.

Tablet Oral Solid Dosage Form

A compound of the invention or a pharmaceutically-acceptable salt thereof (40 g) is thoroughly blended with microcrystalline cellulose (445 g), silicon dioxide fumed (10 g), and stearic acid (5 g). The mixture is then compressed on a tablet press to form tablets weighing 100 mg each. Each tablet provides 8 mg of the active agent per unit dose suitable for oral administration.

Tablet Oral Solid Dosage Form

A compound of the invention or a pharmaceutically-acceptable salt thereof (10 g) is thoroughly blended with cornstarch (50 g), crosscarmellose sodium (25 g), lactose (110 mg), and magnesium stearate (5 mg). The mixture is then compressed on a tablet press to form tablets weighting 200 mg each. Each tablet provides 10 mg of the active agent per unit dose suitable for oral administration.

Capsule Oral Solid Dosage Form

A compound of the invention or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 4 mg, 10 mg or 20 mg active agent per capsule.

Powder in Capsules

A compound of the invention or a pharmaceutically-acceptable salt thereof (1 to 50 mg) is filled into an empty hydroxypropyl methylcellulose (HPMC) capsule intended for oral administration.

Liquid Formulation

A compound of the invention or a pharmaceutically-acceptable salt thereof (50 mg) is mixed with and fully dissolved in 100 mL low calorie mixed berry sport drink in a capped bottle. Various volumes of this solution are measured out to provide different dose levels.

Liquid Formulation

A liquid formulation comprising a compound of the invention (0.1%), water (98.9%) and ascorbic acid (1.0%) is formed by adding a compound of the invention to a mixture of water and ascorbic acid.

Enteric Coated Oral Dosage Form

A compound of the invention is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the tradenames Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 5 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Utility

The present compounds have been designed to deliver two efficacious agents directly to their site of action in the gastrointestinal tract for the treatment of gastrointestinal inflammatory diseases, in particular for the treatment of inflammatory bowel diseases such as ulcerative colitis (including proctosigmoiditis, pancolitis, ulcerative proctitis and left-sided colitis) and Crohn's disease. The compounds are also expected to be useful for the treatment of colitis associated with immune checkpoint inhibitor therapies. In particular, the thiocarbamate glucuronide prodrugs of the invention are designed to take advantage of the abundance of bacterial β-glucuronide enzyme in the gastrointestinal tract, in particular in the colon, to release the JAK inhibitor tofacitinib predominantly in the lower gastrointestinal tract. The thiocarbamate glucuronide prodrug moiety is also designed to release COS which is converted in vivo to $H_2S$. Generating both $H_2S$ and tofacitinib at their site of action may provide additive and possibly synergistic effects in the treatment of the gastrointestinal inflammatory disorders.

The compounds of the invention are designed to have poor systemic absorption, thus minimizing the risk of immunosuppression. Targeted delivery of $H_2S$ may also avoid the potential toxicity associated with systemic exposure to $H_2S$.

The present prodrug compounds are designed to lack biological activity. For example, the compound of formula 1 is expected to have no significant affinity for, or potency at, the Janus kinase (JAK) family of enzymes, non-JAK enzymes, or a range of G-protein coupled receptors, ion channels and transporters which may be expressed in the gastrointestinal (GI) tract or systemically. Biological activity following administration of the present compounds is attributable to generated tofacitinib.

Compound 1 was shown to release tofacitinib in an oral pharmacokinetics assay in mice (Assay 9). Tofacitinib was found to be present in the colon following oral dosing of compound 1, whereas low levels were found in the plasma. The Colon/Plasma ratio of 366 demonstrates that following oral dosing, compound 1 exhibited a significantly higher exposure of tofacitinib in the colon than exposure in plasma. Additionally, Assay 11 demonstrates the ability of compound 1 to release $H_2S$ in an in-vitro model.

As disclosed in U.S. application Ser. No. 15/358,462 (Theravance Biopharma), the release of tofacitinib from the carbamate analogs of the present compounds upon oral dosing has been studied in mouse, rat, and cynomolgus monkeys. It was shown that the carbamate prodrugs exhibited a significantly higher exposure of tofacitinib in the colon than exposure in plasma. In particular, the release of tofacitinib from the carbamate analog of the compound of formula 1 in specific segments of the gastrointestinal tract was studied in rat and monkey and compared with the concentration obtained from oral dosing of tofacitinib itself at equivalent doses. Not only did the carbamate analog of compound 1 exhibit a significantly higher exposure throughout the gastrointestinal tract than exposure in plasma (for example, ratios greater than 500 in mice and between about 60 and 150 in monkey in colon segments) but also showed an increase in the GI tissue concentration and in the GI tissue to plasma concentration ratio relative to that obtained from oral dosing of tofacitinib itself.

Efficacy of certain carbamate analogs of the compounds of the invention was also tested in the oxazolone-induced colitis model in mice. The carbamate analogs of compounds of formula 1 and 4 demonstrated activity in the oxazolone-induced colitis model in mice at lower oral doses than required by direct administration of tofacitinib to achieve an equivalent effect. In addition, the efficacious doses of the carbamate analog of compound 1 are associated with reduced systemic exposure of tofacitinib relative to the systemic exposure obtained from dosing tofacitinib itself at its efficacious dose. In a model of immunosuppression in mice, the carbamate analog of compound 1 demonstrated minimal effect of immunosuppression at the same dose required to demonstrate comparable efficacy in the oxazolone model (therapeutic index>3-fold) whereas tofacitinib is immunosuppressive at a dose lower than its efficacious dose (therapeutic index≤0.3).

Accordingly, the thiocarbamate glucuronide prodrugs of tofacitinib of the invention are expected to be useful for the treatment of inflammatory bowel disease, in particular ulcerative colitis. The present compounds are also expected to be useful for the treatment of Crohn's disease and for the treatment of colitis associated with immune checkpoint inhibitor therapy, a potentially serious consequence of cancer immunotherapies. Immune checkpoint inhibitor therapies include, but are not limited to, cytotoxic T lymphocyte associated antigen 4 (CTLA-4) inhibitors, such as ipilimumab (Yervoy®) and tremelimumab; programmed cell death 1 (PD-1) inhibitors, such as pembrolizumab (Keytruda®) and nivolumab (Opdivo®); and programmed death ligand 1 (PD-L1) inhibitors, such as atezolizumab (Tecentriq®), durvalumab, and avelumab. In particular, the compounds are expected to be useful for the treatment of CTLA-4 inhibitor-induced colitis. The compounds may also find utility in the treatment of additional conditions such as the gastrointestinal adverse effects in graft versus host disease (such as graft versus host disease-related colitis), celiac sprue, microscopic colitis, pouchitis, autoimmune enteropathy, collagenous colitis, lymphocytic colitis, Behcet's disease, celiac disease, ileitis, eosinophilic esophagitis, and infectious colitis.

In one aspect, therefore, the invention provides a method of treating a gastrointestinal inflammatory disease in a mammal (e.g., a human), the method comprising administering to the mammal a therapeutically-effective amount of a compound of the invention or of a pharmaceutical composition comprising a pharmaceutically-acceptable carrier and the compound of the invention.

In one embodiment, the gastrointestinal inflammatory disease is ulcerative colitis. In another embodiment, the gastrointestinal inflammatory disease is Crohn's disease. And in another embodiment, the gastrointestinal inflammatory disease is colitis associated with immune checkpoint inhibitor therapy.

The invention further provides a method of treating ulcerative colitis in a mammal, the method comprising administering to the mammal a therapeutically-effective amount of a compound of the invention or of a pharmaceutical composition comprising a pharmaceutically-acceptable carrier and a compound of the invention.

When used to treat ulcerative colitis, the compound of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 2 to about 60 mg/day of the compound of formula (I), including from about 4 to about 50 mg/day and from about 4 to about 40 mg per day for an average 70 kg human.

Combination Therapy

Compounds of the invention may also be used in combination with one or more agents which act by the same mechanism or by different mechanisms to effect treatment of gastrointestinal inflammatory disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin $α_4β_7$ antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the present compounds include, but are not limited to, mesalamine, olsalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-alpha4 antibodies, such as natalizumab, anti-integrin $α_4β_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.).

Other compounds that may be used in combination with the compounds of the invention include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, *Trichuris suis* ova, K(D)PT, midismase, DNVX-078, vatelizumab, alequel, low molecular weight heparin, metenkefalin, tridecactide, HMPL-004, SB-012, olsalazine, balsalazide, propionyl-L-carnitine, *Clostridium butyricum*, beclomethasone and acemannan.

In another aspect, therefore, the invention provides a therapeutic combination for use in the treatment of gastrointestinal inflammatory disorders, the combination comprising a compound of the invention and one or more other therapeutic agents useful for treating gastrointestinal inflammatory disorders. For example, the invention provides a combination comprising a compound of the invention and one or more agents selected from aminosalicylates, steroids, systemic immunosuppressants, anti-TNFα antibodies, anti-alpha4 antibodies, anti-integrin $α_4β_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the invention.

Further, in a method aspect, the invention provides a method of treating gastrointestinal inflammatory disorders, the method comprising administering to the mammal a compound of the invention and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Ac=acetyl
ACN=acetonitrile
alloc=allyloxycarbonyl
d=day(s)
DCM=dichloromethane
DIPEA=N,N-diisopropylethylamine
DMAP=4-dimethylaminopyridine
Et$_3$N=triethylamine
EtOAc=ethyl acetate
EtOH=ethanol
h=hour(s)
IPA=isopropyl alcohol
MeOH=methanol
min=minute(s)
RT=room temperature
tBu=tert-butyl
TFA=trifluoroacetic acid
THF=tetrahydrofuran
NH$_2$=amino Reagents and solvents were or can be purchased from commercial suppliers (Sigma-Aldrich, Fluka, etc.), and used without further purification. Progress of reaction mixtures were or can be monitored by thin layer chromatography (TLC), analytical high performance liquid chromatography (anal. HPLC), and mass spectrometry. Reaction mixtures were or can be worked up as described specifically in each reaction; commonly they were or can be purified by extraction and other purification methods such as temperature-, and solvent-dependent crystallization, and precipitation. In addition, reaction mixtures were or can routinely be purified by column chromatography or by preparative HPLC, typically using C18 or BDS column packings and conventional eluents. Typical preparative HPLC conditions are described below.

Characterization of reaction products were or can routinely be carried out by mass spectrometry and analytical HPLC. Mass spectrometric identification of compounds were or can be performed by an electrospray ionization method (ESMS) with an Applied Biosystems (Foster City, Calif.) model API 150 EX instrument or a Waters (Milford, Mass.) 3100 instrument, coupled to autopurification systems.

| Preparative HPLC Conditions | |
| --- | --- |
| Column: | C18, 5 μm. 21.2 × 150 mm or C18, 5 μm 21 × 250 or C14, 5 μm 21 × 150 mm |
| Column temperature: | Room Temperature |
| Flow rate: | 20.0 mL/min |
| Mobile Phases: | A = Water + 0.05% TFA B = ACN + 0.05% TFA, |
| Injection volume: | (100-1500 μL) |
| Detector wavelength: | 214 nm |

Crude compounds were or can be dissolved in 1:1 water:acetic acid at about 50 mg/mL. A 4 minute analytical scale test run was or can be carried out using a 2.1×50 mm C18 column followed by a 15 or 20 minute preparative scale run using 100 μL injection with the gradient based on the % B retention of the analytical scale test run. Exact gradients are typically sample dependent. Samples with close running impurities were or can be checked with a 21×250 mm C18 column and/or a 21×150 mm C14 column for best separation. Fractions containing desired product can typically be identified by mass spectrometric analysis.

Analytical HPLC Conditions
Method A
Instrument: Agilent 1260 HPLC
Column: LUNA C18 (2), 150×4.60 mm, 3 micron
Column temperature: 35° C.
Flow rate: 1.2 mL/min
Injection volume: 5 μL
Sample preparation: Dissolve in 1:1 ACN:water to ~0.5 mg/mL solution
Mobile Phases: A=Water:ACN:TFA (98:2:0.05)
B=Water:ACN:TFA (30:70:0.05)
Detector wavelength: 230 nm
Gradient: 28 min total (time (min)/% B): 0/10, 20/100, 22/100, 23/10, 28/10
Method B
Instrument: Agilent 1260 HPLC
Column: Zorbax-Bonus RP C14, 30×2.1 mm, 1.8 micron
Column temperature: 60° C.
Flow rate: 1.2 mL/min
Injection volume: 3 μL
Sample preparation: Dissolve in 1:1 ACN:water to ~1.0 mg/mL solution
Mobile Phases: A=Water:TFA (99.9%:0.1%)
B=ACN:TFA (99.9%:0.1%)
Detector wavelength: 214 nm
Gradient: 3.0 min total (time (min)/% B): 0/5, 1.5/65, 1.8/95, 2.1/95, 2.5/5, 3.0/5

Preparation 1 (2S,3R,4S,5S,6S)-2-(4-(hydroxymethyl)-2-nitrophenoxy)-6-(methoxycarbonyl)tetrahydro-2H-pyran-3,4,5-triyl triacetate (10)

(a) (2S,3R,4S,5S,6S)-2-(4-formyl-2-nitrophenoxy)-6-(methoxycarbonyl)tetrahydro-2H-pyran-3,4,5-triyl triacetate (9)

To a 2 L 3-neck flask equipped with a mechanical stirrer was added (2R,3R,4S,5S,6S)-2-bromo-6-(methoxycarbonyl)tetrahydro-2H-pyran-3,4,5-triyl triacetate (8) (51 g, 128.4 mmol), 4-hydroxy-3-nitrobenzaldehyde (20.98 g, 125.5 mmol), and silver oxide (37.7 g, 162.7 mmol), followed by ACN (750 mL). The reaction mixture was stirred in the dark for 18 h and filtered through diatomaceous earth (Celite®). The solid was washed with ACN (3×100 mL) and the filtrate was distilled under reduced pressure to 100 mL. To the filtrate was added EtOAc (1750 mL) and sat. sodium bicarbonate (1 L) and the reaction mixture was stirred at RT for 30 min, filtered through Celite and allowed to settle. The organic layer was washed with sat. sodium bicarbonate (1 L) and brine (1 L), dried over sodium sulfate (100 g) for 2 h, filtered and distilled under reduced pressure to dryness to provide crude Compound 9 as a yellow solid (55 g, 90% yield, 97.4% purity) HPLC Retention time 15.61 min.

(b) (2S,3R,4S,5S,6S)-2-(4-(hydroxymethyl)-2-nitrophenoxy)-6-(methoxycarbonyl)tetrahydro-2H-pyran-3,4,5-triyl triacetate (10)

To a 1 L 3-neck flask equipped with a mechanical stirrer was added Compound 9 (32.7 g, 67.6 mmol) followed by DCM (350 mL) and IPA (70 mL). The reaction mixture was stirred to dissolve the solid and then cooled to 0° C. To the solution was added sodium borohydride (1.54 g, 40.6 mmol) in three portions, keeping the temperature below 5° C., and the reaction mixture was stirred at 0° C. for 1 h and slowly poured into ice water (400 mL). To the solution was added DCM (350 mL) and the mixture was stirred for 30 min, allowed to settle for 30 min and the layers were separated. The aqueous layer was back extracted with DCM (100 mL). The combined organic layers were washed with brine (500 mL). After 30 min, the layers were separated and the brine layer was back extracted with DCM (100 mL). The combined organic layers were dried over sodium sulfate (50 g) for 2 h, filtered through Celite, and distilled under reduced pressure to dryness. The resulting solid was stirred with 95% denatured EtOH (130 mL) at 50° C. for 30 min and at RT for 12 h to form a crystalline solid which was washed with EtOH (30 mL) and dried under vacuum at RT for 16 h to provide the title compound as a white solid (21 g, 66% yield 98% purity) HPLC Method A Retention time 13.18 min.

Preparation 2: (2S,3S,4S,5R,6S)-2-(methoxycarbonyl)-6-(4-(((methyl(2-(methylamino)ethyl)carbamothioyl)oxy)methyl)-2-nitrophenoxy)tetrahydro-2H-pyran-3,4,5-triyl triacetate, AcOH (12a)

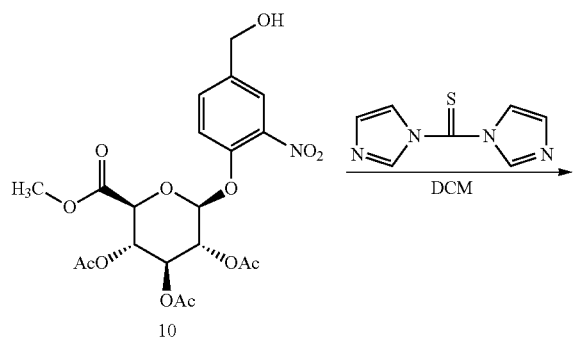

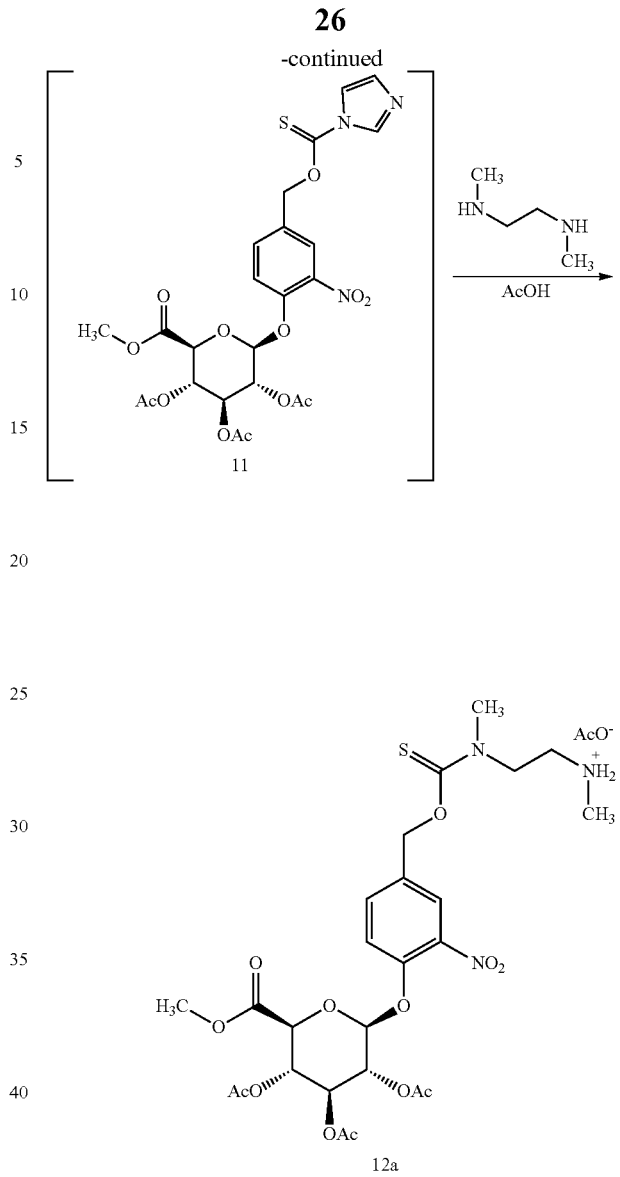

To a 10 mL 1-neck flask equipped with magnetic stirrer was added 10 (1.00 g, 2.06 mmol) and DCM (3.5 mL). The solution was cooled to 0-5° C., and 1,1'-thiocarbonyldiimidazole (0.477 g, 2.68 mmol) was added. The reaction mixture was stirred at 0-5° C. for 4 h to form intermediate 11 ((2S,3R,4S,5S,6S)-2-(4-(((1H-imidazole-1-carbonothioyl)oxy)methyl)-2-nitrophenoxy)-6-(methoxycarbonyl)tetrahydro-2H-pyran-3,4,5-triyl triacetate). In a separate 50 mL 1-neck reaction flask equipped with magnetic stirrer, acetic acid (413 µL, 7.21 mmol) was added slowly to a solution of N,N'-dimethylethylenediamine (0.768 mL, 7.21 mmol) in DCM (7.5 mL) at 0-5° C. to form a suspension. The solution of intermediate 11 was added to this suspension dropwise via cannula and stirred at 0-5° C. for 3 h. The reaction mixture was transferred to a 100 mL 1-neck flask, diluted with DCM (50 mL), and quenched with $H_2O$ (30 mL). The layers were separated, and the organic layer was washed twice with $H_2O$, then brine and was subsequently dried over $Na_2SO_4$ and filtered. The resulting solution of the title compound 12a in DCM was stored overnight at −20° C. and used without further purification. (m/z): [M+H$^+$] calculated for $C_{25}H_{34}N_3O_{13}S$ 616.18 found 616.3.

Preparation 3: (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-nitrophenoxy)-6-(methoxycarbonyl)tetrahydro-2H-pyran-3,4,5-triyl triacetate (14)

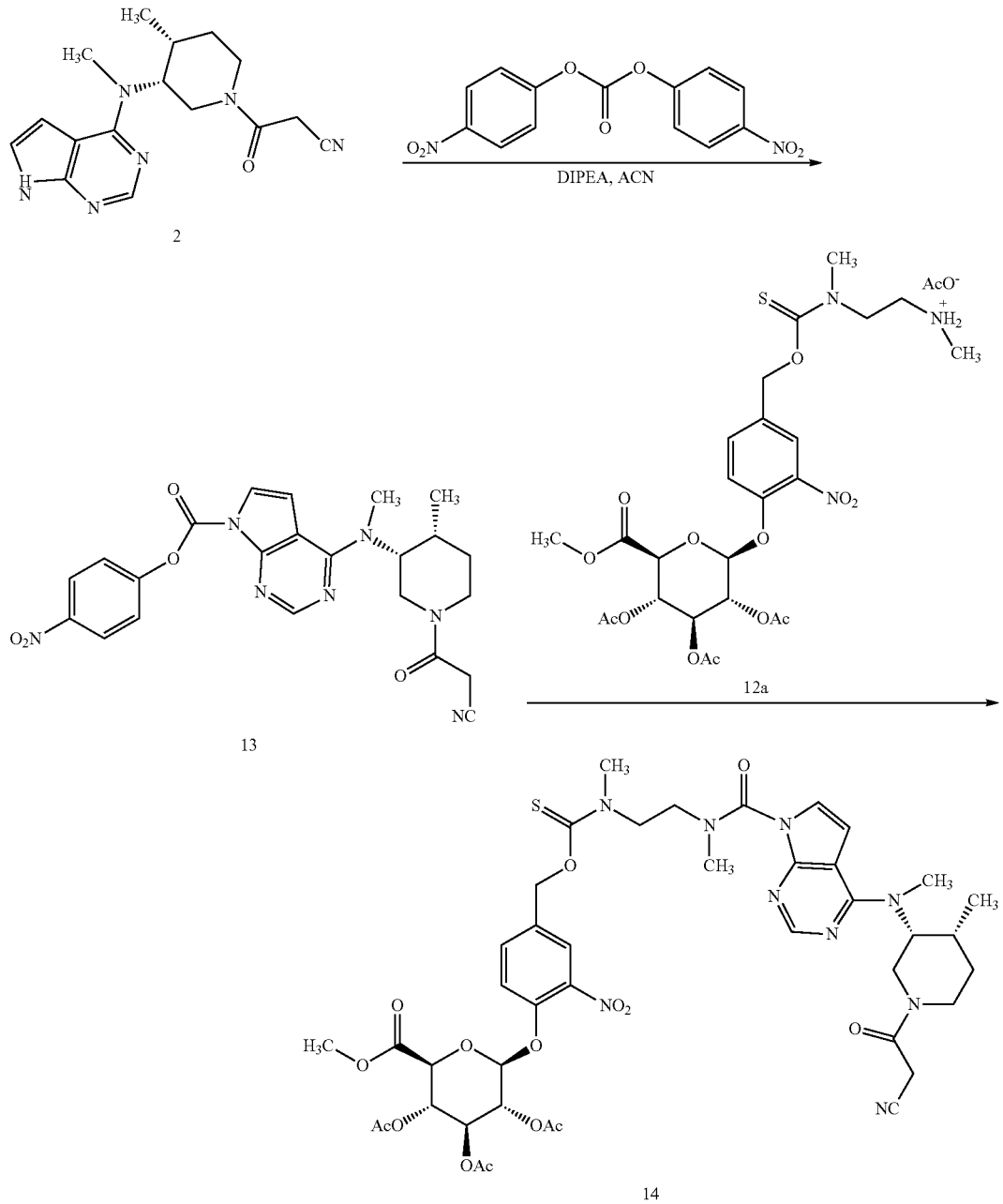

To a 50 mL 1-neck flask equipped with magnetic stirrer was added 3-((3R,4R)-4-methyl-3-(methyl(7H-pyrrolo[2,3-d]pyrimidin-4-yl)amino)piperidin-1-yl)-3-oxopropanenitrile 2 (0.312 g, 1.00 mmol), bis(4-nitrophenyl) carbonate (0.411 g, 1.35 mmol), and acetonitrile (8.0 ml), and the solution was cooled to 0-5° C. DIPEA (0.24 ml, 1.4 mmol) was added, and the reaction mixture was stirred at RT for 4 h. The reaction mixture containing compound 13 formed in this reaction was cooled to 0-5° C. and (2S,3S,4S,5R,6S)-2-(methoxycarbonyl)-6-(4-(((methyl(2-(methylamino)ethyl)carbamothioyl)oxy)methyl)-2-nitrophenoxy)tetrahydro-2H-pyran-3,4,5-triyl triacetate, AcOH 12a in DCM (30 mL, 1.0 mmol) was added dropwise. The reaction mixture was stirred at 0-5° C. for 1 h before being quenched with acetic acid (80 μL, 1.4 mmol). The mixture was diluted with DCM (25 mL), transferred to a separating funnel, and washed with H$_2$O, NaHCO$_3$ (satd. aq.), and brine. The organic layer was dried over Na$_2$SO$_4$, filtered, and concentrated. Purification by reverse-phase column chromatography (10-95% H$_2$O/CH$_3$CN) afforded the title compound 14 (0.218 g, 0.229 mmol, 91% purity, 23% yield). (m/z): [M+H]$^+$ calcd for C$_{42}$H$_{52}$N$_9$O$_{15}$S 954.33 found 954.0.

Example 1: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-nitrophenoxy)-3,4,5-trihydroxytetrahydro-2H-pyran-2-carboxylic acid (1)

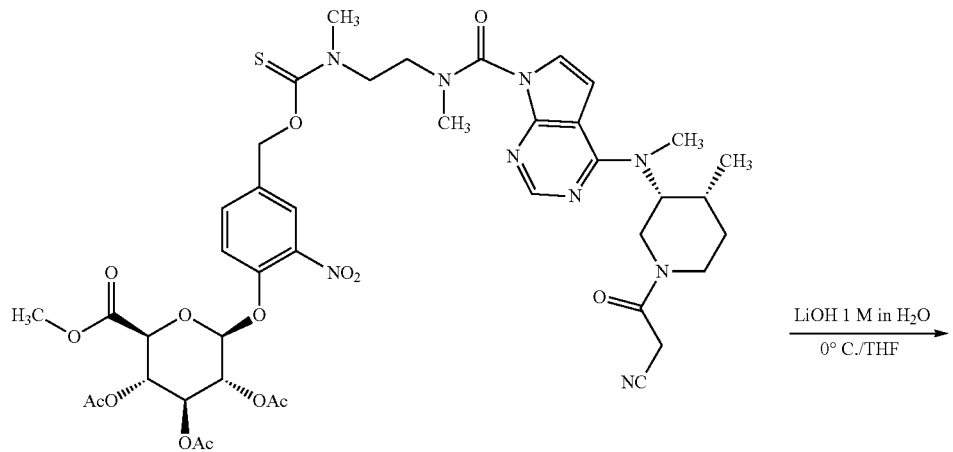

14

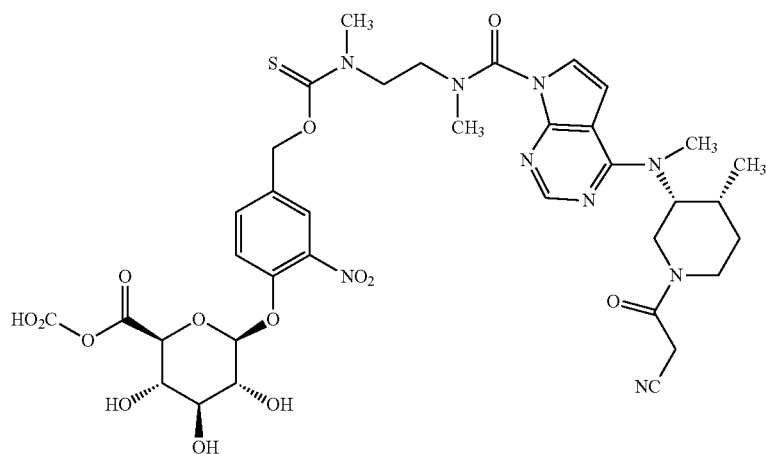

1

To a 10 mL 1-neck flask equipped with magnetic stirred was added (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-nitrophenoxy)-6-(methoxycarbonyl)tetrahydro-2H-pyran-3,4,5-triyl triacetate 14 (0.210 g, 0.220 mmol) and THF (2.2 mL), and the solution was cooled to 0-5° C. LiOH (1 M aq., 0.463 mL, 0.463 mmol) was added, and the reaction mixture was stirred at 0-5° C. for 20 min. LiOH (1 M aq., 0.463 mL, 0.463 mmol) was added, and the reaction mixture was stirred at 0-5° C. for a further 2 h. Acetic acid (52.5 μL, 0.924 mmol) was added, and the mixture was concentrated. Purification by reverse-phase column chromatography (5-95% $H_2O/CH_3CN$) afforded the title compound 1 (0.110 g, 0.135 mmol, 99% purity, 61% yield). (m/z): [M+H$^+$] calcd for $C_{35}H_{43}N_9O_{12}S$ 814.28 found 814.3. $^1$H NMR (600 MHz, DMSO-d$_6$) δ 8.24 (dd, J=12.5, 3.7 Hz, 1H), 7.92 (app s, 1H), 7.71 (app d, J=8.5 Hz, 1H), 7.43 (m, 1H), 7.22 (m, 1H), 6.81 (app s, 1H), 5.49 (m, 2H), 5.27 (m, 1H), 4.80 (app s, 1H), 3.91-4.17 (m, 3H), 3.60-3.90 (m, 4H), 3.38-3.54 (m, 2H), 3.26-3.38 (m, 5H), 2.76-3.26 (m, 5H), 2.38 (m, 1H), 1.79 (m, 1H), 1.58 (m, 1H), 1.02 (d, J=6.5 Hz, 3H).

Example 2 (2S,3S,4S,5R,6S)-6-(2-amino-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-3,4,5-trihydroxytetrahydro-2H-pyran-2-carboxylic acid (3)

Analogously to the methods described in U.S. application Ser. No. 15/358,462 (Theravance Biopharma), (2S,3R,4S,5S,6S)-2-(2-amino-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-6-(methoxycarbonyl)tetrahydro-2H-pyran-3,4,5-triyl triacetate (15) may be

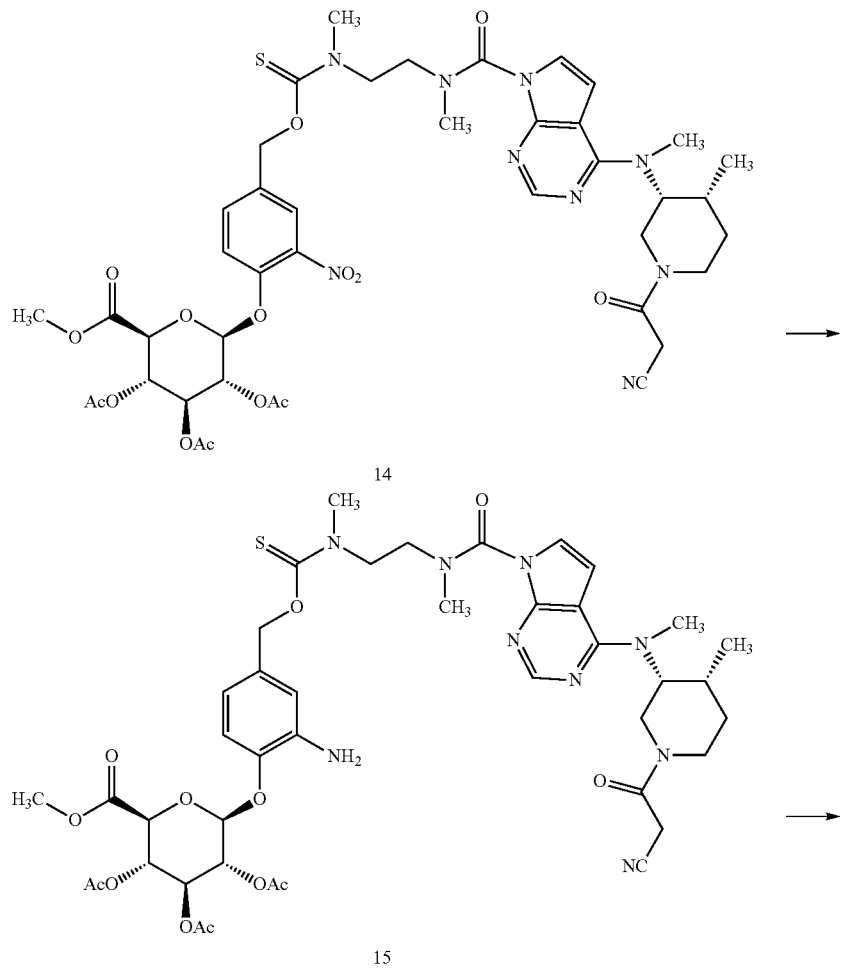

14

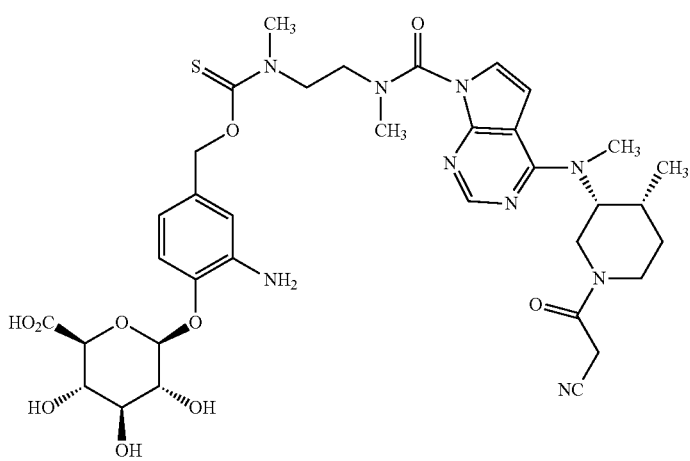

3 formed by reduction of the nitro group of compound (14), for example by using palladium hydroxide on carbon. (2S, 3S,4S,5R,6S)-6-(2-amino-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl) (methyl)carbamothioyl)oxy)methyl)phenoxy)-3,4,5-trihydroxytetrahydro-2H-pyran-2-carboxylic acid (3) may be obtained by deprotection of compound (15) under hydrolyzing conditions, for example by using a base like LiOH.

Preparation 4: 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13)

To a solution of 3-((3R,4R)-4-methyl-3-(methyl(7H-pyrrolo[2,3-d]pyrimidin-4-yl)amino)piperidin-1-yl)-3-oxopropanenitrile (2) (0.75 g, 2.40 mmol) in DCM (12 mL) was added a solution of sodium hydroxide (0.29 g, 7.20 mmol) in water (4.00 mL) and tetrabutylammonium bromide (0.08 g, 0.24 mmol). A solution of 4-nitrophenyl chloroformate (0.97 g, 4.80 mmol) in DCM (4 mL) was slowly added. The reaction mixture was stirred at RT for 1 h, extracted with DCM, and the organic layer was washed with satd. ammonium chloride solution and brine, dried over sodium sulfate, filtered and concentrated in vacuo. The crude residue was purified by column chromatography (0-100% EtOAc in hexanes) to afford title compound (0.94 g, 82%) as a light yellow solid. (m/z): [M+H]+ calcd for $C_{23}H_{23}N_7O_5$ 478.18 found 478.2.

Preparation 5: (2S,3S,4S,5R,6S)-2-(methoxycarbonyl)-6-(4-(((methyl(2-(methylamino)ethyl)carbamothioyl)oxy)methyl)phenoxy)tetrahydro-2H-pyran-3,4,5-triyl triacetate (18)

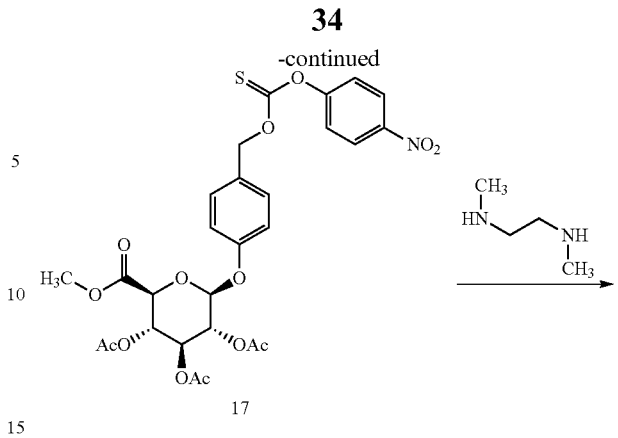

Analogously to the methods described in U.S. application Ser. No. 15/358,462 (Theravance Biopharma), (2S,3S,4S,5R,6S)-2-(methoxycarbonyl)-6-(4-((((4-nitrophenoxy)carbonothioyl)oxy)methyl) phenoxy)tetrahydro-2H-pyran-3,4,5-triyl triacetate (17) may be obtained by reaction of (2S, 3R,4S,5S,6S)-2-(4-(hydroxymethyl)phenoxy)-6-(methoxycarbonyl)tetrahydro-2H-pyran-3,4,5-triyl triacetate (16) with p-nitrophenyl chlorothioformate in presence of a base in a solvent like DCM. Compound (17) may be isolated, optionally purified and reacted with $N^1,N^2$-dimethylethane-1,2-diamine in a solvent such as DCM to form (2S,3S,4S,5R,6S)-2-(methoxycarbonyl)-6-(4-(((methyl(2-(methylamino)ethyl)carbamothioyl)oxy) methyl)phenoxy)tetrahydro-2H-pyran-3,4,5-triyl triacetate (18).

The following intermediates can be prepared by a process analogous to Preparation 5 with the appropriate substituents and starting materials:

| R[1] | Compound No. |
|---|---|
| methyl | 19 |
| chloro | 20 |
| methoxy | 21 |

Intermediates 18, 19, 20 and 21 may also be prepared by a process analogous to the one described in Preparation 1 and 2 with the appropriate substituents and starting materials.

Example 3: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-3,4,5-trihydroxytetrahydro-2H-pyran-2-carboxylic acid (4)

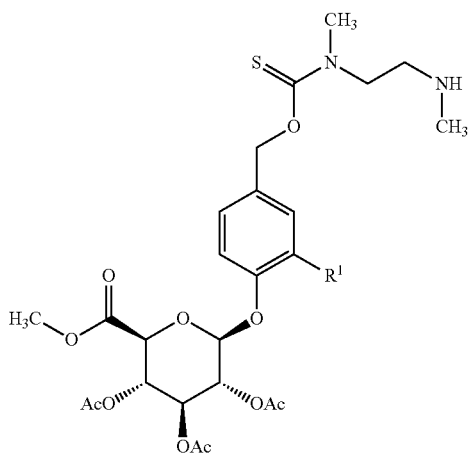

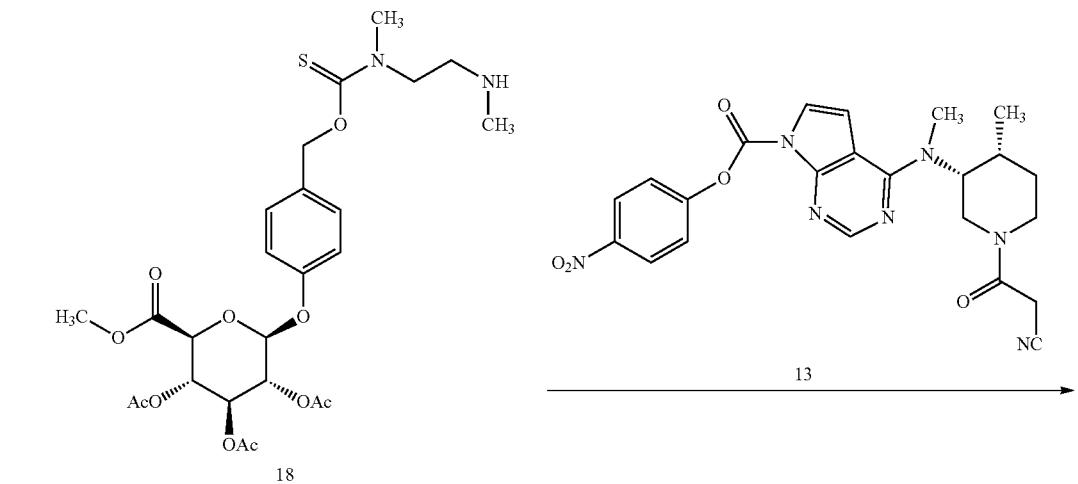

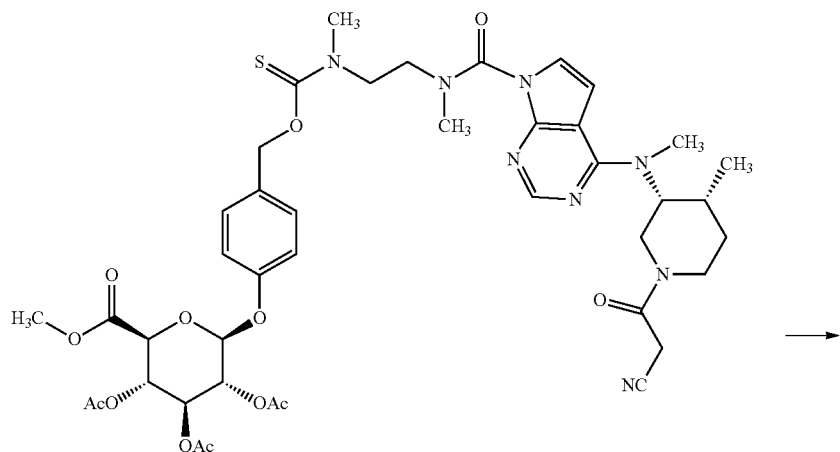

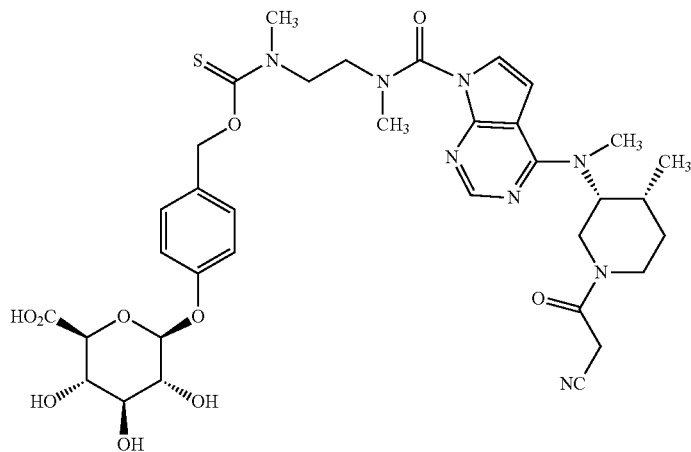

4

Analogously to the methods described in Preparation 3 and Example 1, as well as in U.S. application Ser. No. 15/358,462 (Theravance Biopharma), (2S,3R,4S,5S,6S)-2-(4-((((2-(4-(43R,4R)-1-(2-cyanoacetyl)-4-methylpiperidin-3-yl)(methyl)amino)-N-methyl-7H-pyrrolo[2,3-d]pyrimidine-7-carboxamido)ethyl)-(methyl)carbamothioyl)oxy)methyl)phenoxy)-6-(methoxycarbonyl)tetrahydro-2H-pyran-3,4,5-triyl triacetate (22) may be formed by reacting (2S,3S,4S,5R,6S)-2-(methoxycarbonyl)-6-(4-(((methyl(2-(methylamino)ethyl)carbamothioyl)oxy)methyl)phenoxy) tetrahydro-2H-pyran-3,4,5-triyl triacetate (18) and 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) in presence of a base such as trimethylamine and in a solvent such as DCM. (22) may be isolated and hydrolyzed, for example in presence of a base such as LiOH, to form compound (4).

Example 4: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-methylphenoxy)-3,4,5-trihydroxytetrahydro-2H-pyran-2-carboxylic acid
(5)

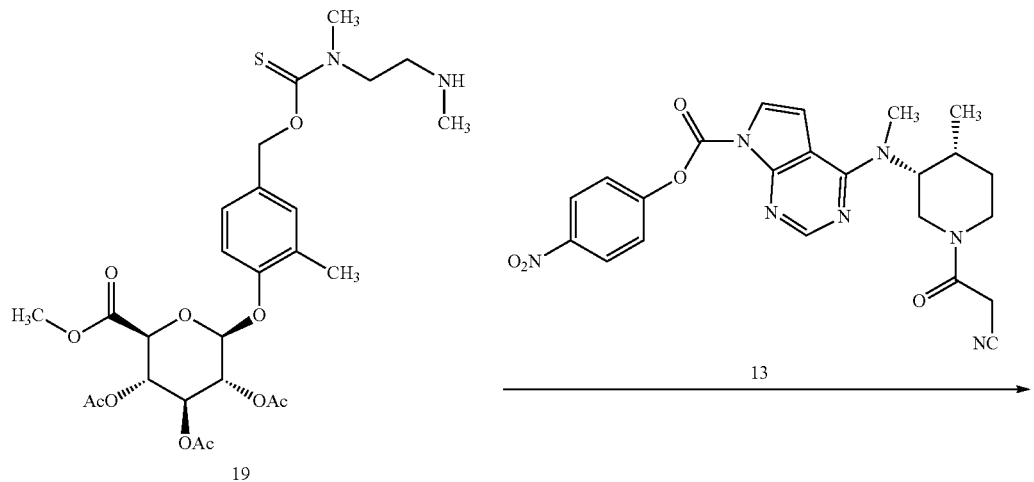

-continued

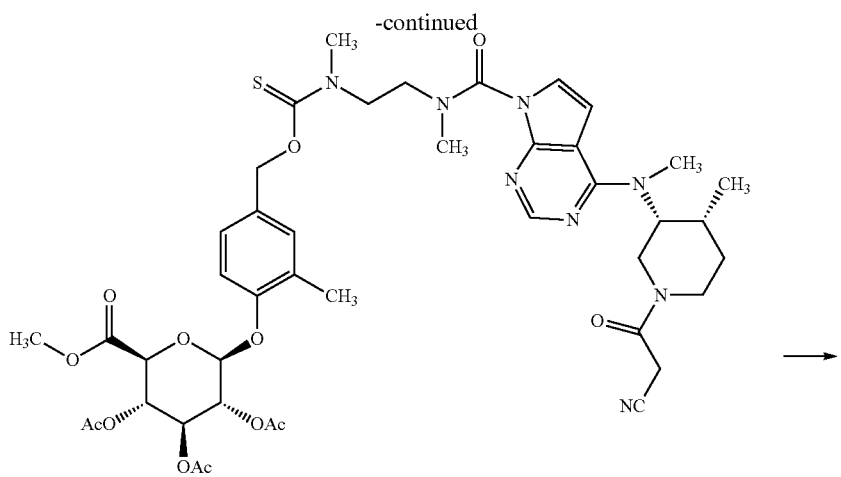

23

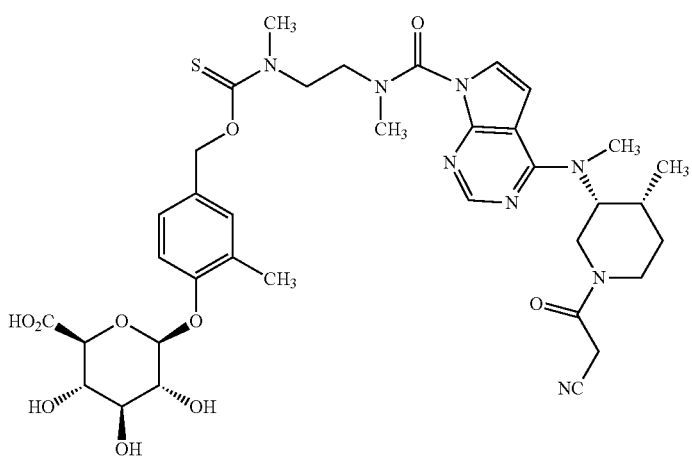

5

Analogously to the methods described in Preparation 3 and Example 1, as well as in U.S. application Ser. No. 15/358,462 (Theravance Biopharma), (2S,3R,4S,5S,6S)-2-(4-((((2-(4-(43R,4R)-1-(2-cyanoacetyl)-4-methylpiperidin-3-yl)(methyl)amino)-N-methyl-7H-pyrrolo[2,3-d]pyrimidine-7-carboxamido)ethyl)-(methyl)carbamothioyl)oxy)methyl)-2-methylphenoxy)-6-(methoxycarbonyl)tetrahydro-2H-pyran-3,4,5-triyl triacetate (23) may be prepared by reacting (2S,3S,4S,5R,6S)-2-(methoxycarbonyl)-6-(2-methyl-4-(((methyl(2-(methylamino)ethyl)carbamothioyl)oxy)methyl)phenoxy)tetrahydro-2H-pyran-3,4,5-triyl triacetate (19) with 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) in a solvent such as DCM. Compound (23) may be isolated and hydrolyzed to remove the protecting groups with for example a base such as LiOH to give (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-methylphenoxy)-3,4,5-trihydroxytetrahydro-2H-pyran-2-carboxylic acid (5).

Example 5: (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-3,4,5-trihydroxytetrahydro-2H-pyran-2-carboxylic acid (6)
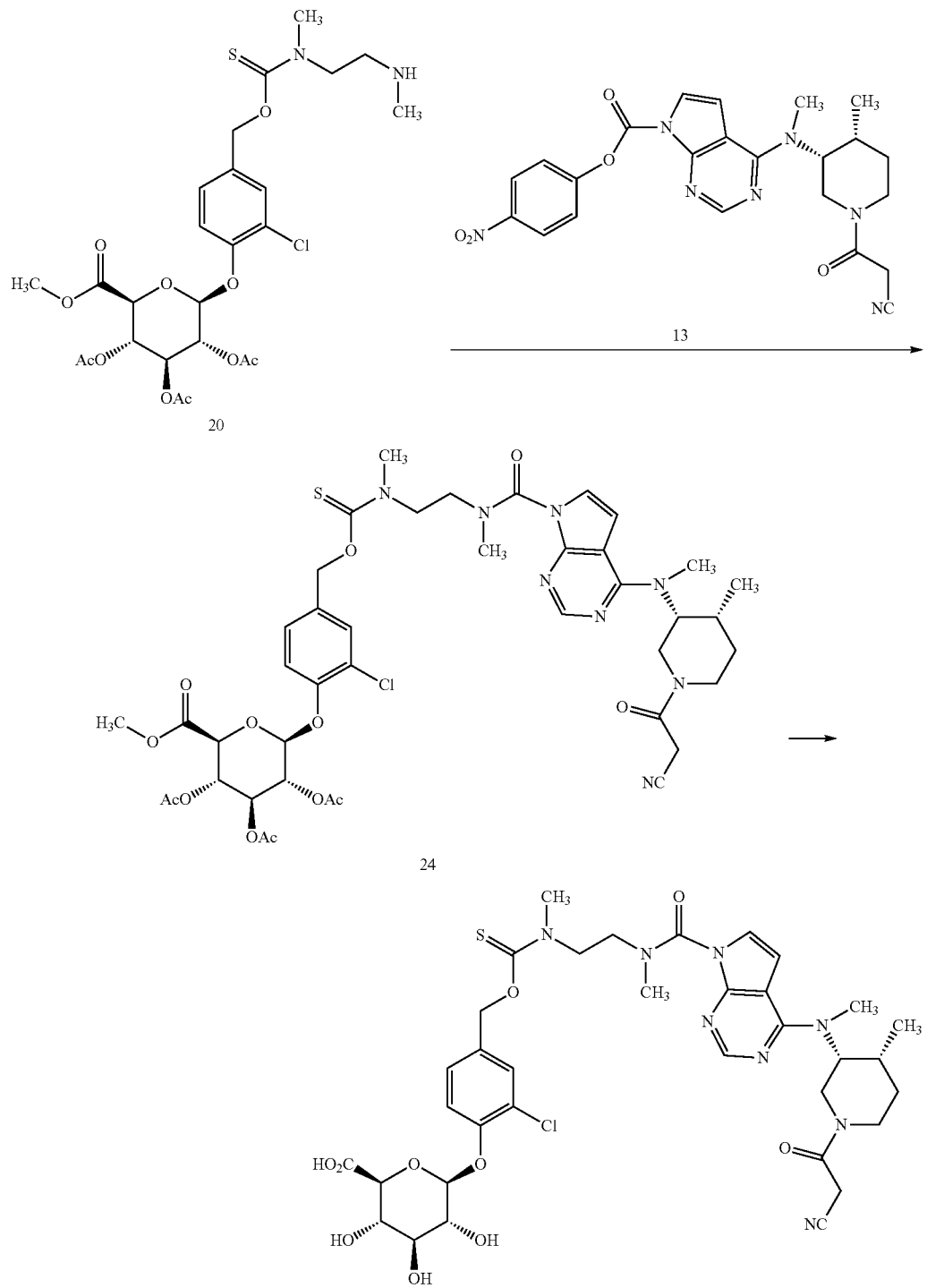

Analogously to the methods described in Preparation 3 and Example 1, as well as in U.S. application Ser. No. 15/358,462 (Theravance Biopharma), (2S,3R,4S,5S,6S)-2-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-6-(methoxycarbonyl)tetrahydro-2H-pyran-3,4,5-triyl triacetate (24) may be prepared by reacting (2S,3R,4S,5S,6S)-2-(2-chloro-4-(((methyl(2-(methylamino)ethyl)-carbamothioyl)oxy)methyl)phenoxy)-6-(methoxycarbonyl)tetrahydro-2H-pyran-3,4,5-triyl triacetate (20) and 4-nitrophenyl 4-(((3R,4R)-1-(2-cyanoacetyl)-4-methylpiperidin-3-yl)(methyl)amino)-7H-pyrrolo[2,3-d]pyrimidine-7-carboxylate (13) in the presence of a base such as Et₃N. Compound (24) may be isolated and hydrolyzed to remove the protecting groups with, for example, a base such as LiOH, to give (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)phenoxy)-3,4,5-trihydroxytetrahydro-2H-pyran-2-carboxylic acid (6)

Example 6: (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy)methyl)-2-methoxyphenoxy)-3,4,5-trihydroxytetrahydro-2H-pyran-2-carboxylic acid (7)

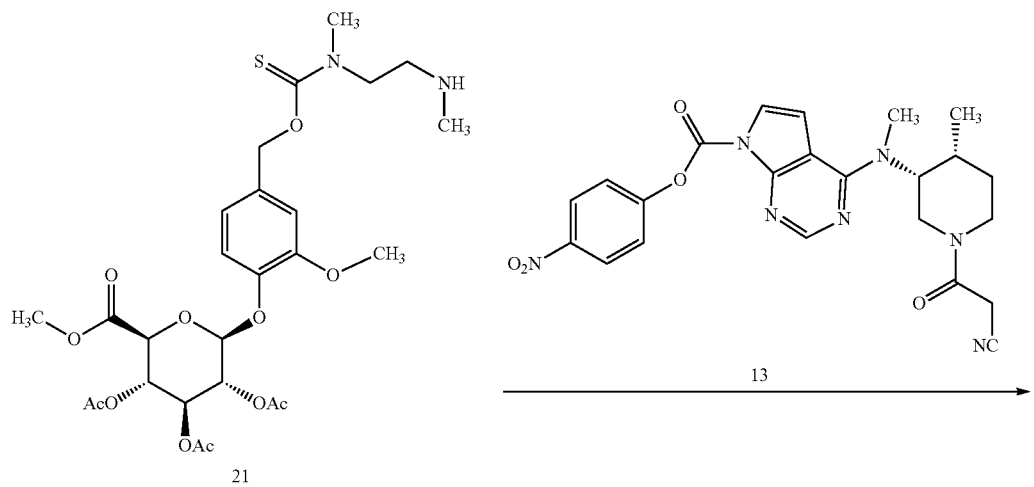

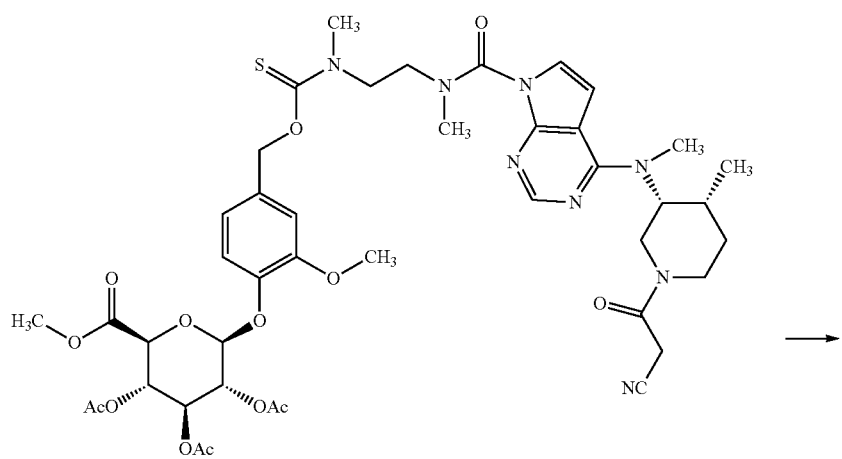

-continued

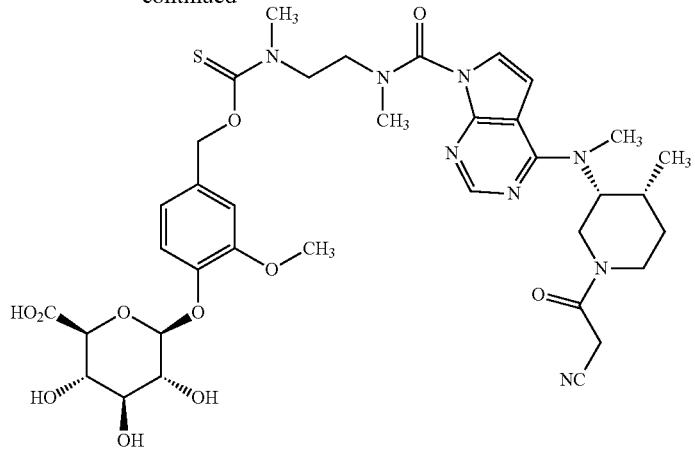

7

Analogously to the methods described in Preparation 3 and Example 1, as well as in U.S. application Ser. No. 15/358,462 (Theravance Biopharma), (2S,3R,4S,5S,6S)-2-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamothioyl)oxy) methyl)-2-methoxyphenoxy)-6-(methoxycarbonyl) tetrahydro-2H-pyran-3,4,5-triyl triacetate (25) may be prepared by reacting (2S,3R,4S,5S,6S)-2-(2-methoxy-4-(((methyl(2-(methylamino)ethyl)carbamothioyl)oxy) methyl)phenoxy)-6-(methoxycarbonyl)tetrahydro-2H-pyran-3,4,5-triyl triacetate (21) with 4-nitrophenyl 4-(((3R, 4R)-1-(2-cyanoacetyl)-4-methylpiperidin-3-yl)(methyl) amino)-7H-pyrrolo[2,3-d]pyrimidine-7-carboxylate (13) in a solvent such as DCM.

Compound (13) may be isolated and hydrolyzed to remove the protecting groups with, for example, a base such as LiOH, to give (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido) ethyl)(methyl)carbamothioyl)oxy)methyl)-2-methoxyphenoxy)-3,4,5-trihydroxytetrahydro-2H-pyran-2-carboxylic acid (7).

Biological Assays

The compounds of the invention can be characterized in one or more of the following biological assays. In the assay descriptions, the compound of formula 1 may alternatively be referenced as compound 1 and similarly for the additional compounds of the invention.

Assay 1: Biochemical JAK Kinase Assay

A panel of four LanthaScreen JAK biochemical assays (JAK1, 2, 3 and Tyk2) can be carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate can be obtained from Life Technologies.

Serially diluted compounds can be pre-incubated with each of the four JAK enzymes and the substrate in white 384-well microplates (Corning) at ambient temperature for 1 h. ATP can subsequently be added to initiate the kinase reactions in 10 pt total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. The JAK1 kinase activity can also be tested at 1 mM ATP concentration. Kinase reactions are allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) are added. The plates are allowed to incubate at ambient temperature for 1h before being read on the EnVision reader (Perkin Elmer). Emission ratio signals (520 nm/495 nm) are recorded and utilized to calculate the percent inhibition values based on DMSO and background controls.

For dose-response analysis, percent inhibition data is plotted vs. compound concentrations, and $IC_{50}$ values are determined from a 4-parameter robust fit model with the Prism software (GraphPad Software). Results are expressed as $pIC_{50}$ (negative logarithm of $IC_{50}$) and subsequently converted to $pK_i$ (negative logarithm of dissociation constant, Ki) using the Cheng-Prusoff equation.

Assay 2: Metabolic Stability in β-Glucuronidase from *E. coli*

To characterize the intermediate metabolites and final product of a compound of the invention, in the presence of β-glucuronidase enzyme, a compound of the invention (30 µM in DMSO) can be incubated at 37° C. in the presence of purified β-glucuronidase from *E. coli* (100 Units/mL in a 0.1 M potassium phosphate buffer) over a time course of 0-90 minutes. The incubations are quenched at timepoints 0, 1, 2, 3, 5, 10, 15, 30, 60, and 90 min by addition of 100 µL of ACN. Samples are diluted with water+1% formic acid (4×) and analyzed using a Thermo Q-Exactive™ LC-MS system. The compound and tofacitinib concentrations are quantified by comparison with standard curves determined using the same dilutions as the samples.

To demonstrate that the observed conversion of the compound tested to tofacitinib is due to glucuronidase enzyme interaction, the compound (30 µM) can be incubated with β-glucuronidase (45 Units/mL) and the known bacterial β-glucuronidase inhibitor amoxapine (100 µM). After a 60 min incubation, the final concentration of tofacitinib can be determined in the presence of the inhibitor as compared with absence of inhibitor.

Assay 3: Metabolic Stability in Homogenates Prepared from Rat Upper and Lower Intestinal Content The conversion of a compound of the invention to tofacitinib can be evaluated in the intestinal lumen content prepared from the various GI segments isolated from freshly sacrificed rats. Each segment of content from the duodenum, jejunum, ileum, and colon is diluted 1:10 in Dulbecco's phosphate buffer saline (DPBS) solution. A 10 mM DMSO stock of the compound tested is diluted into DPBS to yield a final substrate concentration of 10 µM. The incubation is conducted in a water bath at 37° C. and time points are taken at 0, 5, 10, 20, 40 and 60 min. The total incubation volume is 400 µL and 40 µL aliquots are taken at each time point and diluted into 160 µL of 97% ACN+3% formic acid+an internal standard. The samples are centrifuged at 2200 rcf for 10 min and 50 µL of supernatant was diluted into 150 µL of water+1% formic acid. The samples are analyzed on an API 4000 mass spectrometer for the compound tested and tofacitinib.

Assay 4: Oral Pharmacokinetics in Rat

The objective of this study is to compare the gastrointestinal mucosal and plasma pharmacokinetics of the compound tested and tofacitinib following a simultaneous oral dose. Male Sprague Dawley rats (n=3/time point) are dosed via oral gavage with the compound tested and a dose normalized of trideuterium labeled tofacitinib ($D_3$-tofacitinib) formulated as a solution in 5% DMSO+1% hydroxypropyl methyl cellulose in water. At each time point (0.5, 1, 3, 6, 8 and 24 h), plasma samples are taken by cardiac puncture and the following tissues are collected: stomach, upper gastrointestinal tract (sectioned approximately into thirds [U-1, U-2, U-3]). cecum, and lower gastrointestinal tract (sectioned approximately into halves [L-1, L-2]). Each tissue sample is rinsed with water, patted dry, transferred to a tared container, weighed, diluted with 3 times the weight of tissue by volume (w/v) with acidified water, homogenized at 6500 RPM (3×45 sec), and frozen. Concentrations of tofacitinib released from the compound tested and of $D_3$-tofacitinib in each tissue sample can be determined as follows. The tissue samples are vortexed, combined with a 50 µL aliquot of rat plasma, extracted with 200 µL of ACN containing an internal standard and quantified against the internal standard by LC-MS. Concentrations of tofacitinib released from the compound tested are measureable in plasma between 3 and 8 hours, in the stomach and sections U-1, U-2, and U-3 through 8 hours, and in the cecum, and sections L-1, and L-2 between 3 and 24 hours. Concentrations of $D_3$-tofacitinib can be measured in plasma between 0.5 and 8 hours, in the stomach and sections U-1, U-2, and U-3 through 8 hours, and in the cecum, and sections L-1, and L-2 between 3 and 24 hours. The resulting standard pharmacokinetic parameters, $C_{max}$ (maximum concentration) and AUC (0-t) (area under the curve of concentration vs. time, integrated to the last time point measured) can be reported.

Assay 5: Oral Pharmacokinetics in Cynomolgus Monkey

The objective of this study is to compare the colonic and plasma pharmacokinetics of the compound tested and tofacitinib following a simultaneous oral dose. Male cynomolgus monkeys (n=1/time point) are dosed via oral gavage with the compound tested and trideuterium labeled tofacitinib ($D_3$-tofacitinib) formulated as a solution in 98.5% pH 6 citrate buffer+1% hydroxypropyl methylcellulose+0.5 Tween 20. At each time point (0.5, 1, 3, 6, 9 and 24 h), plasma samples are taken from the femoral vein and the following tissues are collected: stomach, upper gastrointestinal tract (sectioned approximately into thirds [U-1, U-2, U-3]). cecum, proximal colon, distal colon, and rectum. Each tissue sample is rinsed with water, patted dry, transferred to a tared container, weighed, flash frozen, pulverized, and stored at −70° C. An approximately 2 g aliquot is diluted 3 times the weight of tissue by volume (w/v) with control rat plasma in water, homogenized, and stored at −70° C. Concentrations of tofacitinib released from the compound tested and of $D_3$-tofacitinib in each tissue sample are determined as follows. The samples are vortexed, and a 50 µL aliquot of plasma or prepared tissue sample is extracted with 200 µL of ACN containing an internal standard and quantified against the internal standard by LC-MS. Concentrations of tofacitinib released from the compound tested are measureable in plasma and all tissue samples between 0.5 and 24 hours. Concentrations of $D_3$-tofacitinib are measureable in plasma and stomach between 0.5 and 9 hours, and in all other tissue sections between 0.5 and 24 hours. The resulting standard pharmacokinetic parameters, $C_{max}$ (maximum concentration) and AUC (0-t) (area under the curve of concentration vs. time, integrated to the last time point measured) can be reported.

Assay 6: Mouse Model of Oxazolone-Induced Colitis

Oxazolone-induced colitis is an experimental model that has a histological resemblance to human ulcerative colitis (Heller et al. *Immunology*, 2002, 17, 629-638). Adult BALB/C mice (25-28 g, 9-12 weeks of age) from BioNeeds (India) are used in the assay. On day 1, animals are lightly anesthetized with isoflurane and the hairs between the shoulder are carefully removed before oxazolone (6 mg/mouse, 100 µL, 4:1 acetone: olive oil formulation) or vehicle solution is slowly applied for skin sensitization. Six days after skin sensitization, the mice are fasted overnight, anesthetized with ketamine and xylazine administered IP, and a 1 mL syringe filled with oxazolone solution, is inserted carefully ~3.8 cm into the colon of the mouse. Animals are kept in a head down position and oxazolone (0.5 mg/50 µL/mouse in 50% ethanol) or 50% ethanol/saline is rectally instilled very slowly over a minute. The mice are held vertically (head down) for another minute to ensure that the entire oxazolone solution remained inside the colon. Drug treatment (PO, BID or TID) or vehicle is initiated the evening prior to the oxazolone intrarectal (IR) challenge. On both first (Day 1) and second (Day 2) days post-oxazolone IR challenge, the Disease Activity Index (DAI) is assessed by treatment-blinded experimenters for each mouse, according to the following subscores: stool consistency (0, normal; 2, loose; 4, diarrhea), gross bleeding and hemoccult test (0, absence; 2, blood tinged; 4, overt blood presence), and weight loss (0, none; 1, 1%-5%; 2, 6%40%; 3, 11%-15%; 4, more than 15%); DAI=average of (stool consistency+blood presence+weight loss scores).

An area-under-the-curve (AUC) calculation based on total DAI scores is performed to track disease progression during the course of the experiment. AUC for each experimental group is calculated as: AUC=[(Day 1−Day 0)*Average (DAI Score of Day 0 & Day 1)]+[(Day 2−Day 1)*Average (DAI Score of Day 1 & Day 2)]. A Student's t-test can be used to compare the DAI AUC score of the vehicle/vehicle and vehicle/oxazolone groups to evaluate whether disease is induced following oxazolone treatment. This is followed by a one way ANOVA, with Dunnett's post hoc test, to compare the DAI AUC score of the vehicle/oxazolone and test compound/oxazolone groups.

Assay 7: Immunosuppression Effects in Mouse Splenic Natural Killer (NK) Cells

Depletion of mouse splenic cells is an experimental model of immunosuppression (Kudlacz et al., *Am. J. of Transplan-*

*tation*, 2004, 4, 51-57). A compound can be assessed in the mouse splenic cell model following the same treatment paradigm as that used in the oxazolone-induced colitis model (Assay 6).

Adult male Balb/C mice (12-14 weeks of age) from Harlan are used for the study. The compound tested and tofacitinib at various doses are administered orally for three days to naïve mice. Spleens are harvested 30 min or 3 h post last dose and crushed immediately for cell subtype staining. Prior to fixation, fluorophore-labelled antibodies for CD19 (FITC; B cells), CD3e (PE; pan T cells) and DX5 (APC; NK cells) are incubated with splenocyte samples from each animal to allow for simultaneous, multiple subtype % analysis on the flow cytometer. The number of total spleen cells for each animal is measured by Scepter™ 2.0 Handheld Automated Cell Counter.

The absolute number of lymphocyte subtype population (e.g., splenic B, T and NK cells) is calculated from the percentage of each subtype times total spleen cells for each animal. A one way ANOVA, with Dunnett's post hoc test, is used to compare the splenic lymphocytes number of the vehicle and test compound groups.

This assay can show whether the compound affects splenic NK cell counts or not.

This assay, in conjunction with anti-colitic effect in the mouse model of oxazolone-induced colitis (Assay 6), allows determination of a functional therapeutic index.

Assay 8: Rat Colon Fecal Homogenate Stability

The objective of this study is to determine the stability of the present compounds in rat colon fecal homogenate, i.e. the half-life for decomposition in the presence of the β-glucuronidase in rat colon feces.

Following sacrifice of a naïve male rat (~300 g) by cardiac puncture exsanguination, the colon is ligated and removed to an anaerobic chamber (AS-580, Anaerobe Systems). The fecal content is removed within the chamber and diluted 1:10 (1 gram to 9 mL phosphate buffer) and then homogenized using a handheld Omni Tissue Master. The fecal homogenate is centrifuged at 2000 g for 10 min to remove bulk and the supernatant is removed and used for the incubations.

Test articles and a positive control (sulfasalazine) are prepared as 10 mM DMSO stocks. The final substrate concentration of each assay is 10 µM. Reactions are started by adding a 5 µL aliquot of diluted test compound stock into 300 µL of rat fecal supernatant-homogenate. At 0, 15, 30, 60, 90, and 120 min post reaction initiation, a 50 µL aliquot is removed into 200 µL of acetonitrile with 3% formic acid and an internal standard molecule. All samples are centrifuged at 2000 g for 10 min after which 50 µL of supernatant is diluted into 150 µL of water for analysis on an LC-MS system. In vitro half-lives for loss of pro-drug are calculated as follows: (T½=0.693/elimination rate constant).

Assay 9: Oral Pharmacokinetics in Mouse

The object of this study is to assess the plasma and colon conversion of prodrugs of the invention to tofacitinib following oral dosing in mice.

Male Balb/c mice (n=2/timepoint) receive a single PO oral gavage dose (for example 5 mg/kg in 1:20 mixture of 5% DMSO and 1 HPMC) of test compounds. At 2 hr and 6 hr post dosing mice are sacrificed via cardiac puncture exsanguination, resulting blood samples are placed into Microtainer® tubes containing NaF and then placed on ice. Plasma is obtained by centrifugation (eppendorf centrifuge, 5804R) for 4 min at approximately 12,000 rpm at 4° C.

The colons are removed from exsanguinated mice and the colon fecal contents gently removed. The colons are flushed with saline and patted dry. They are then homogenized in 3× volume of sterile water using a Precellys homogenizer at approximately 4° C. All samples are stored at −80° C. for later bioanalysis.

Concentrations of tofacitinib released from prodrug in each tissue sample are determined as follows: the plasma and colon homogenate samples are vortexed, combined with a 50 µL aliquot of rat plasma, extracted with 200 µL of ACN containing an internal standard and quantified against the internal standard by LC-MS. An area under the concentration curve ($AUC_{0-6}$ hr) is calculated for plasma and colon test compound and liberated tofacitinib. The key parameter to assess suitability is tofacitinib colon/plasma AUC ratio.

Compound 1

The object of this study was to assess the plasma, colon and fecal conversion of compound 1 to tofacitinib following oral dosing in mice.

Male Balb/c mice (n=3/timepoint) received a single PO oral gavage dose of compound 1 (5 mg/kg in 1% HPMC with 0.1% Tween 80). At 0.5, 1, 3, 6 and 24 hr post oral dosing, mice were sacrificed via cardiac puncture exsanguination, resulting blood samples were placed into Microtainer® tubes containing NaF and then placed on ice. Plasma was obtained by centrifugation (eppendorf centrifuge, 5804R) for 4 min at approximately 12,000 rpm at 4° C.

The colons were removed from exsanguinated mice and the colon fecal contents gently removed. The colons were flushed with saline and patted dry. They were then homogenized in 3× volume of sterile water using a bead homogenizer at approximately 4° C. The colon contents of these animals were homogenized using 9 volumes of sterile water. All samples were stored at −80° C. for later bioanalysis.

Concentrations of tofacitinib released from compound 1 in each tissue sample were determined as follows: the plasma, colon or fecal content homogenate samples were vortexed, combined with a 50 µL aliquot of rat plasma, extracted with 200 µL of ACN containing an internal standard and quantified against the internal standard by LC-MS-MS. An area under the concentration curve ($AUC_{0-24}$ hr) was calculated for plasma, colon and feces content of compound 1 and the liberated tofacitinib.

TABLE 1

| Tofacitinib Concentration in Mouse | | | |
|---|---|---|---|
| Compound No. | Plasma AUC (µg * hr/mL) | Colon AUC (µg * hr/g) | Colon/Plasma Ratio |
| 1 | 0.0198 | 7.26 | 366 |

Assay 10: Oral Pharmacokinetics in Rat

The object of this study is to assess the plasma and colon conversion of prodrugs of the invention to tofacitinib following oral dosing in rats.

Male Sprague Dawley rats (n=2/timepoint) receive a single PO oral gavage dose (for example 5 mg/kg in 1:20 mixture of 5% DMSO and 1 HPMC) of test compounds. At 0.5, 1, 3, 6 and 24 hr post dosing rats are sacrificed via cardiac puncture exsanguination, resulting blood samples are placed into Microtainer® tubes containing NaF and then placed on ice. Plasma is obtained by centrifugation (Eppendorf centrifuge, 5804R) for 4 minutes at approximately 12,000 rpm at 4° C.

The colons are removed from exsanguinated rats and the colon contents gently removed. The colons are flushed with saline and patted dry. They are then homogenized in 3× the weight of sterile water using a Precellys homogenizer at approximately 4° C. All samples are stored at −80° C. for later bioanalysis.

Concentrations of tofacitinib released from prodrug in each tissue sample are determined as follows: the plasma and colon samples are vortexed, combined with a 50 μL aliquot of rat plasma, extracted with 200 μL of ACN containing an internal standard and quantified against the internal standard by LC-MS. An area under the concentration curve ($AUC_{0-6}$ hr) is calculated for plasma and colon test compound and liberated tofacitinib. The key parameter to assess suitability is tofacitinib colon/plasma AUC ratio.

Assay 11: Release of $H_2S$ and Tofacitinib

The object of this study was to demonstrate the release of $H_2S$ from the thiocarbamate pro-drug compound 1 in an in-vitro model.

The method used to detect $H_2S$ was previously described in Tan et al., *Nature Scientific Reports,* 2017, 7:46278, DOI: 10.1038/srep46278.

Compound 1 (50 μM) was incubated with β-glucuronidase (100 units/mL) and monobromobimane (MBB, 100 μM) in potassium phosphate buffer pH 7.4 (100 mM) for 60 min at 37° C. In addition, incubations were carried out with and without a) β-glucuronidase and b) MBB as negative control. Incubation of SN38-Glucuronide was also carried out with β-glucuronidase as a positive control for β-glucuronidase activity. The reactions were terminated at 60 min by the addition of three volumes of ice-cold acetonitrile to the incubation mixture. The incubation samples were centrifuged (4° C., 2200×g, 10 minutes) and the supernatants were transferred to amber HLPC vials. All samples were stored at 4° C. until the analysis. The samples were analyzed using a Thermo Orbitrap LC-MS/MS system.

The protonated molecular ions of the reaction products with % Peak Area and the retention times are shown in the following Table.

TABLE 2

β-Glucuronidase Reaction Products

| β-glucuronidase Reaction Products of compound 1 | Retention Time (min) | $(M + H)^+$ | % (MS Peak Area) (60 min) |
|---|---|---|---|
| compound 1 (Parent) | 13.6 | 814.2825 | 0 |
| Tofacitinib | 10.3 | 313.1771 | 79.7 |
| Imidazolidinone derivative (e) | 8.9 | 115.0866 | 14.5 |
| SDB (Sulfide Dibimane) | 14.5 | 415.1435 | 5.9 |

The results of the analysis demonstrated that the test compound was hydrolyzed to form tofacitinib, the imidazolidinone derivative (e), and hydrogen sulfide. $H_2S$ was trapped using monobromobimane (MBB) to form sulfide dibimane (SDB).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula (I):

(I)

wherein n is 0, 1 or 2;

$R^1$ is selected from hydrogen, $C_{1-4}$ alkyl, $C_{1-3}$ alkoxy, amino, nitro, halo, cyano, hydroxy, and trifluoromethyl;

each $R^2$, when present, is independently selected from $C_{1-4}$ alkyl, $C_{1-3}$ alkoxy, amino, nitro, halo, cyano, hydroxyl, and trifluoromethyl;

$R^3$ is selected from hydrogen, methyl and ethyl;

$R^4$ is selected from hydrogen, methyl and ethyl;

or a pharmaceutically-acceptable salt thereof.

2. The compound of claim 1, wherein $R^1$ is hydrogen.

3. The compound of claim 1, wherein $R^1$ is nitro.

4. The compound of claim 1, wherein $R^1$ is amino.

5. The compound of claim 1, wherein n is 0.

6. The compound of claim 1, wherein n is 1.

7. A compound of formula (II):

(II)

wherein $R^1$ is selected from hydrogen, $C_{1-4}$ alkyl, $C_{1-3}$ alkoxy, amino, nitro, halo, cyano, hydroxy, and trifluoromethyl;

or a pharmaceutically-acceptable salt thereof.

8. The compound of claim 7, wherein $R^1$ is selected from hydrogen, methyl, methoxy, amino, nitro, and chloro.

9. The compound of claim 7, wherein $R^1$ is hydrogen.

10. The compound of claim 7, wherein $R^1$ is amino.

11. A compound of formula 1:

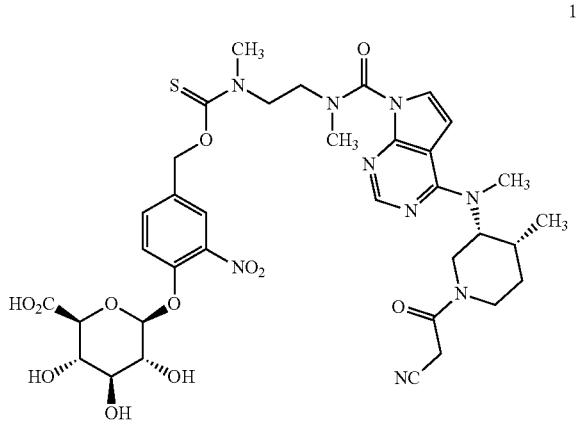 [SMILES: C[C@@H]1CCN(C(=O)CC#N)C[C@@H]1N(C)c1ncnc2c1ccn2C(=O)N(C)CCN(C)C(=S)OCc1ccc(O[C@@H]2O[C@H](C(=O)O)[C@@H](O)[C@H](O)[C@H]2O)c([N+](=O)[O-])c1]

or a pharmaceutically acceptable salt thereof.

12. The compound of claim 11, wherein the compound is (2S,3S,4S,5R,6S)-6-(4-((((2-(4-(((3R,4R)-1-(2-cyano-acetyl)-4-methylpiperidin-3-yl)(methyl)amino)-N-methyl-7H-pyrrolo[2,3-d]pyrimidine-7-carboxamido)ethyl)(methyl) carbamothioyl)-oxy)methyl)-2-nitrophenoxy)-3,4,5-trihydroxytetrahydro-2H-pyran-2-carboxylic acid.

13. A compound of formula 4:

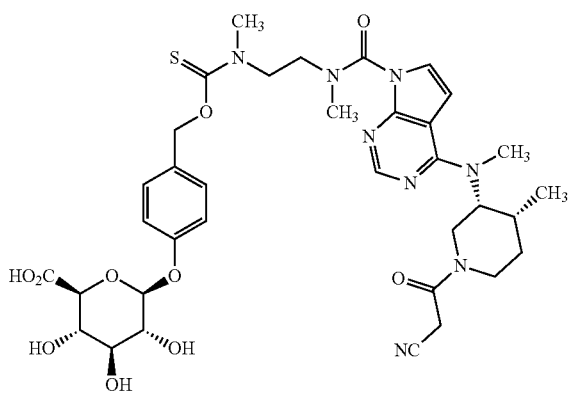

or a pharmaceutically acceptable salt thereof.

14. The compound of claim 13, wherein the compound is (2S,3S,4S,5R,6S)-6-(4-((((2-(4-(((3R,4R)-1-(2-cyano-acetyl)-4-methylpiperidin-3-yl)(methyl)amino)-N-methyl-7H-pyrrolo[2,3-d]pyrimidine-7-carboxamido)ethyl)(methyl) carbamothioyl)-oxy)methyl)phenoxy)-3,4,5-trihydroxytetrahydro-2H-pyran-2-carboxylic acid.

15. The compound of claim 1, wherein upon contact with a β-glucuronidase enzyme, carbonyl sulfide and a compound of formula 2:

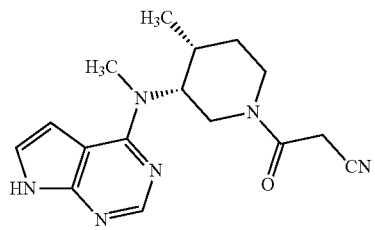

or a salt thereof are produced.

16. A pharmaceutical composition comprising a pharmaceutically acceptable-carrier and a compound of claim 1, 11 or 13, or a pharmaceutically acceptable salt thereof.

17. A process for preparing a compound of claim 1, the process comprising deprotecting a compound of formula (I-A):

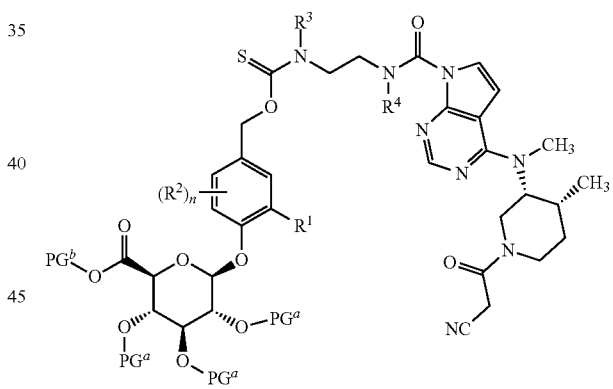

or a salt thereof; wherein $R^1$, $R^2$, $R^3$, $R^4$ and n are as defined in claim 1; each $PG^a$ is independently a hydroxyl protecting group; and $PG^b$ is a carboxyl protecting group; to provide a compound of formula (I) or a pharmaceutically acceptable salt thereof.

18. The process of claim 17, wherein $R^1$ is nitro; $R^3$ and $R^4$ are methyl; each $PG^a$ is acetyl; $PG^b$ is methyl; and n is 0.

19. A process for preparing a compound of claim 11, the process comprising:

(a) reacting a compound of formula 12':

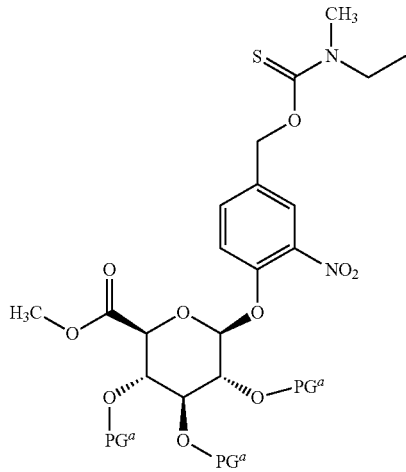

or a salt thereof; wherein each $PG^a$ is independently a hydroxyl protecting group, with a compound of formula 13:

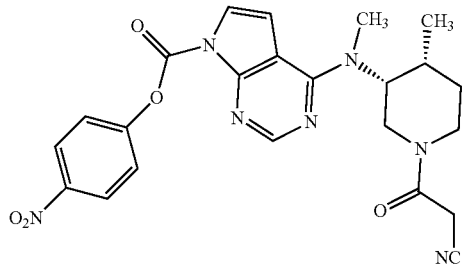

to provide a compound of formula 14':

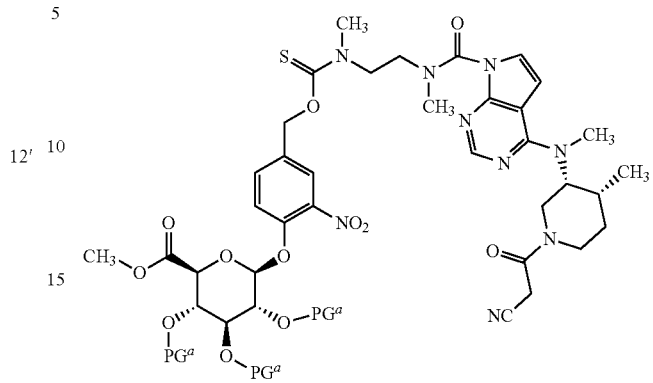

and (b) deprotecting the compound of formula 14' to provide the compound of formula 1 or a pharmaceutically acceptable salt thereof.

20. A method of treating a gastrointestinal inflammatory disease in a mammal, the method comprising administering to the mammal a pharmaceutical composition comprising a pharmaceutically acceptable-carrier and a compound of claim 1, or a pharmaceutically acceptable salt thereof.

21. The method of claim 20, wherein the gastrointestinal inflammatory disease is ulcerative colitis.

22. The method of claim 20, wherein the gastrointestinal inflammatory disease is Crohn's disease.

23. The method of claim 20, wherein the gastrointestinal inflammatory disease is colitis associated with immune checkpoint inhibitor therapy.

24. A method of delivering tofacitinib and $H_2S$ to the colon of a mammal, the method comprising orally administering to the mammal a thiocarbamate-containing prodrug of tofacitinib, or a pharmaceutically acceptable salt thereof, wherein the thiocarbamate-containing prodrug of tofacitinib is cleaved to release tofacitinib and carbonyl sulfide and carbonyl sulfide is further converted to $H_2S$ in vivo.

25. The method of claim 24, wherein the thiocarbamate-containing prodrug of tofacitinib contains a glucuronide moiety.

26. The method of claim 25, wherein the thiocarbamate-containing prodrug of tofacitinib is cleaved by β-glucuronidase in the colon.

27. The method of claim 24, wherein the thiocarbamate-containing prodrug of tofacitinib is a compound of claim 1, or a pharmaceutically acceptable salt thereof.

* * * * *